(12) United States Patent
Fan et al.

(10) Patent No.: US 11,104,909 B2
(45) Date of Patent: Aug. 31, 2021

(54) α-AMYLASE VARIANT AND USE THEREOF

(71) Applicant: NANJING BESTZYME BIO-ENGINEERING CO., LTD., Nanjing (CN)

(72) Inventors: Yan Fan, Nanjing (CN); Xiuzhen Du, Nanjing (CN); Minghui Hao, Nanjing (CN); Yan Sun, Nanjing (CN); Ke Huang, Nanjing (CN); Feng Li, Nanjing (CN)

(73) Assignee: NANJING BESTZYME BIO-ENGINEERING CO., LTD., Nanjing (CN)

( * ) Notice: Subject to any disclaimer, the term of this patent is extended or adjusted under 35 U.S.C. 154(b) by 218 days.

(21) Appl. No.: 16/080,277

(22) PCT Filed: Feb. 24, 2017

(86) PCT No.: PCT/CN2017/074724
§ 371 (c)(1),
(2) Date: Aug. 27, 2018

(87) PCT Pub. No.: WO2017/144008
PCT Pub. Date: Aug. 31, 2017

(65) Prior Publication Data
US 2019/0062764 A1 Feb. 28, 2019

(30) Foreign Application Priority Data

Feb. 26, 2016 (CN) .......................... 201610108232.8

(51) Int. Cl.
*C12N 9/26* (2006.01)
*C12N 9/28* (2006.01)
(Continued)

(52) U.S. Cl.
CPC ............. *C12N 15/75* (2013.01); *C12N 1/205* (2021.05); *C12N 9/2414* (2013.01);
(Continued)

(58) Field of Classification Search
None
See application file for complete search history.

(56) References Cited

U.S. PATENT DOCUMENTS

| 9,267,124 B2 | 2/2016 | Matsui et al. | |
| 2006/0014265 A1* | 1/2006 | Ferrari .................. | C11D 3/386 435/204 |

(Continued)

FOREIGN PATENT DOCUMENTS

| CN | 102388132 A | 3/2012 |
| CN | 103781910 A | 5/2014 |
| WO | WO 2013/184577 A1 | 12/2013 |

OTHER PUBLICATIONS

UniProt Accession No. O31193_GEOSE, published Jan. 1, 1998 (Year: 1998).*
(Continued)

*Primary Examiner* — Richard C Ekstrom
(74) *Attorney, Agent, or Firm* — Klarquist Sparkman, LLP

(57) ABSTRACT

Provided is an α amylase variant obtained by the mutation or deletion of at least one amino acid residue in the amino acid sequence of a parent α amylase, and at the same time, same is an α amylase maintaining the capability of the parent to hydrolyse α-1,4 glycosidic bond, wherein the amino acid sequence homology of the two reaches 95% or more. A series of α amylase variants provided therein have a relatively high catalytic activity under acidic conditions of pH 5.0 and high temperatures of at least 100° C.

5 Claims, 3 Drawing Sheets
Specification includes a Sequence Listing.

(51) Int. Cl.
*C12N 15/75* (2006.01)
*C12P 19/04* (2006.01)
*C12P 19/14* (2006.01)
*C12N 1/20* (2006.01)
*C12R 1/10* (2006.01)

(52) U.S. Cl.
CPC .......... *C12N 9/2417* (2013.01); *C12P 19/04* (2013.01); *C12P 19/14* (2013.01); *C12R 2001/10* (2021.05); *C12Y 302/01001* (2013.01)

(56) References Cited

U.S. PATENT DOCUMENTS

| | | | | |
|---|---|---|---|---|
| 2009/0117642 | A1* | 5/2009 | Power | C12N 9/2417 435/202 |
| 2009/0226569 | A1* | 9/2009 | Ramer | C12N 9/2417 426/48 |
| 2009/0314286 | A1* | 12/2009 | Cuevas | C12N 9/2417 127/38 |
| 2012/0045822 | A1 | 2/2012 | Concar et al. | |
| 2019/0062764 | A1* | 2/2019 | Fan | C12N 15/75 |

OTHER PUBLICATIONS

Gen Bank Accession No. KIP21039.1, published Feb. 9, 2015 (Year: 2015).*
Gen Bank Accession No. PDB: 1W9X_A, published Feb. 1, 2013 (Year: 2013).*
PCT/CN2017/074724 International Search Report (ISR) and Written Opinion dated May 25, 2017 (with English Translation of the ISR) (13 pages).
CN 102388132 A, US 2012-0045822 A1.
CN 103781910 A, U.S. Pat. No. 9,267,124 B2.

* cited by examiner

Concentration of starch slurry (°Bé)

α-AMYLASE VARIANT AND USE THEREOF

CROSS REFERENCE TO RELATED APPLICATIONS

This is the U.S. National Stage of International Application No. PCT/CN2017/074724, filed Feb. 24, 2017, which in turn claims the benefit of China Patent Application No. 201610108232.8, filed Feb. 26, 2016.

FIELD OF THE INVENTION

The present invention relates to the field of enzyme engineering, and in particular to an α-amylase variant and use thereof.

BACKGROUND OF THE INVENTION

In the industry, the hydrolysis of starch starts mainly with α-amylase. The combined application of α-amylases derived from microorganisms and other enzyme species, such as pullulanase, glucoamylase and glucose isomerase, can effectively break down starch macromolecules, and the produced small-molecule polysaccharides or monosaccharides are of great importance in many applications in food manufacturing, grain processing, beer processing, and alcohol production. The α-amylase belongs to saccharifying hydrolase, with a main structural feature of (α/β)8 folding, which contains a special starch substrate binding site with a length of generally no more than 10 saccharide monomers. However, the binding sites of several amylases can work together to perform multi-site binding to successfully cleave starch macromolecules.

The α-amylase can effectively cleave the α-1,4 glycosidic bond in the starch substrate, thereby rapidly reducing molecular weight and viscosity of the starch substrate, and the products are mainly dextrins of different lengths. There are different kinds of α-amylases, and industrial application conditions of these kinds of α-amylases vary greatly depending on the characteristics of the desired products.

The α-amylase (α-1,4-glucan-4-glucanohydrolases, E.C. 3.2.1.1) is effective in hydrolyzing the α-1,4 glycosidic bond in starch and other polysaccharides. In view of the demand for improving enzyme efficiency and reducing production cost during the hydrolysis of starch, the search for α-amylase which can support effective starch liquefaction in different application fields has become an important research area in the academia and industry. At present, the improvements of the enzyme species by using enzyme engineering techniques mainly focus on the improvements of heat resistance, acid-base tolerance performance, and liquefaction effect.

Many α-amylases in plants and microorganisms have been found to have commercial values, mainly including $B.$ $licheniformis$ α-amylase, $B.$ $amyloliquefaciens$ α-amylase and $G.$ $stearothermophilus$ α-amylase, wherein the variants derived from $B.$ $licheniformis$ α-amylase as a template are the most abundant and are most widely used.

In the present invention, in order to meet the needs of industrial production, we used $G.$ $stearothermophilus$ α-amylase as a template to construct a series of α-amylase variants, and improved the application efficiency of the enzyme species. Especially when pH is low and the amount added is reduced, the liquefaction efficiency of the α-amylase variants of the present invention can be comparable to that of the mainstream products in the market.

SUMMARY OF THE INVENTION

An object of the present invention is to provide a series of $G.$ $stearothermophilus$ α-amylase variants, which can increase the liquefaction efficiency and can adapt to the needs of industrial production. In particular, the enzyme activity and other properties of the α-amylase variants of the present invention can be comparable to those of mainstream products in the market under the conditions of a temperature of 100° C. or above and a pH of 5.0.

Another object of the present invention is to provide a gene encoding the α-amylase variant.

Still another object of the present invention is to provide a method for producing the α-amylase variant and use thereof.

The objects of the present invention can be achieved by the following technical solutions:

An α-amylase variant, which is obtained by mutating or deleting at least one amino acid residue in amino acid sequence of a parental α-amylase, while still retaining the ability of the parental α-amylase to hydrolyze an α-1,4 glycosidic bond; and has amino acid sequence homology of 95% or more with the parental α-amylase.

The parental α-amylase is preferably a natural α-amylase, i.e. a bacterial α-amylase, more preferably an α-amylase of any one selected from the group consisting of Backi Bacillus subtilis, B. licheniformis, B. amyloliquefaciens, G. stearothermophilus i Debbra, 1 or $Bacillus$ $cereus$, further more preferably an α-amylase of $B.$ $licheniformis$ or $G.$ $stearothermophilus$, and most preferably an α-amylase of $G.$ $stearothermophilus$.

The full-length gene sequence encoding the α-amylase of $G.$ $stearothermophilus$ is set forth in SEQ ID NO: 1; and the corresponding amino acid sequence is set forth in SEQ ID NO: 2.

The α-amylase variant is preferably obtained by any one of the following, or any combination of the following:

(1) deleting the $1^{st}$ to $5^{th}$ amino acid residues from the N-terminus of the parental α-amylase of $G.$ $stearothermophilus$ and replacing with VN or ANLN;

(2) deleting 27 to 32 amino acid residues from the C-terminus of the parental α-amylase of $G.$ $stearothermophilus$; for example, deleting the $1^{st}$ to $27^{th}$ amino acid residues from the C-terminus; or deleting the $1^{st}$ to $29^{th}$ amino acid residues from the C-terminus; or deleting the $1^{st}$ to $32^{nd}$ amino acid residues from the C-terminus;

(3) deleting the $180^{th}$ and $181^{st}$ amino acid residues from the N-terminus of the parental α-amylase of $G.$ $stearothermophilus$.

The α-amylase variant is further preferably to be added with three amino acid residues of FAN at the C-terminus in addition to any one of above three cases or any combination of the three cases.

The amino acid sequence of the α-amylase variant is further preferably any one selected from the group consisting of SEQ ID NO: 4, SEQ ID NO: 6, SEQ ID NO: 8, SEQ ID NO: 10 and SEQ ID NO: 12.

The nucleotide coding sequence of the α-amylase variant is any one selected from the group consisting of SEQ ID NO: 3, SEQ ID NO: 5, SEQ ID NO: 7, SEQ ID NO: 9 and SEQ ID NO: 11.

A gene encoding the α-amylase variant of the present invention is provided.

Wherein, the gene is preferably any one selected from the group consisting of SEQ ID NO: 3, SEQ ID NO: 5, SEQ ID NO: 7, SEQ ID NO: 9 and SEQ ID NO: 11.

There is provided an expression vector for expressing the α-amylase variant of the present invention, which comprises a gene encoding the α-amylase variant according to claim 8.

Wherein, the expression vector comprises an expression cassette comprised mainly of a natural or synthetic promoter sequence, a natural or synthetic ribosome binding site, a natural or synthetic terminator sequence, and the gene sequence encoding the α-amylase variant of the present invention.

There is provided a recombinant cell for expressing the α-amylase variant of the present invention, which comprises one or more genes encoding the α-amylase variant of the present invention.

Wherein, the host cell of the recombinant cell is preferably selected from a *Bacillus* strain, further preferably *B. licheniformis* or a *Bacillus* strain genetically engineered to inactivate some endogenous proteins; most preferably *B. licheniformis* genetically engineered to inactivate AprE and/or NprE.

There is provided a method for producing the α-amylase variant of the present invention, which comprises the steps of: culturing a recombinant cell containing a gene sequence encoding the α-amylase variant under conditions suitable for the expression of the α-amylase variant, and obtaining the α-amylase variant from the recombinant cell or its culture supernatant.

Also provided is the use of the α-amylase variant of the present invention in hydrolysis of an α-1,4 glycosidic bond of a polysaccharide; preferably in hydrolysis of an α-1,4 glycosidic bond of a polysaccharide under conditions of a high temperature and/or a low pH.

Wherein, the high temperature is preferably 80° C. to 110° C., more preferably 100° C. to 110° C., and the low pH is preferably 5.0 to 5.5.

Beneficial Effects

A series of α-amylase variants provided by the present invention have high catalytic activity under an acidic condition of pH 5.0 and a high temperature of 100° C. or above. The acid resistance and thermal stability of these α-amylase variants are suitable for starch liquefaction.

SEQUENCE LISTING

Figure 1:
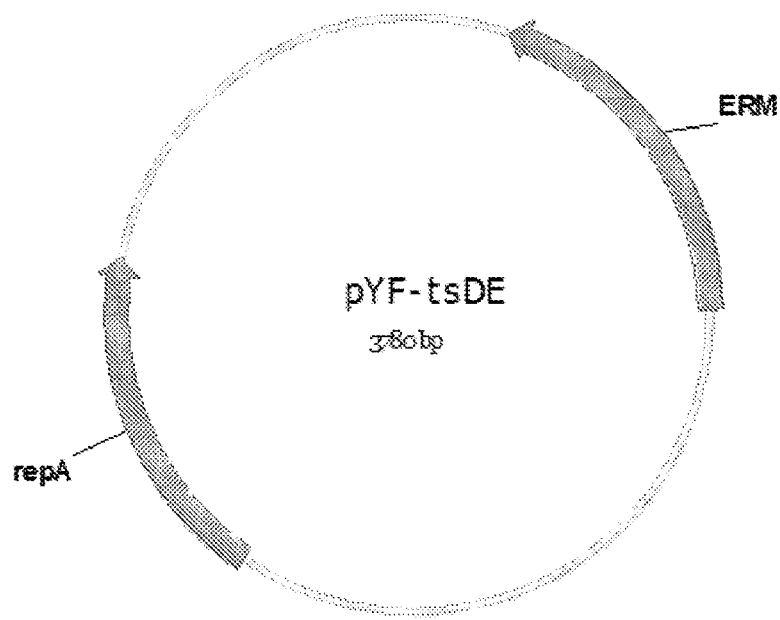
FIG. 1 shows a pYF-tsDE vector, which comprises a temperature-sensitive element (having replication activity at 30° C.) and an erythromycin determinant gene (ErmC), which can tolerate 300 μg/mL erythromycin in *E. coli* and 5 μg/mL erythromycin in *B. licheniformis*. The recombinant host cell containing the nucleotide sequence encoding the α-amylase variant was screened with erythromycin.

The nucleic and amino acid sequences are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The sequence listing submitted herewith, generated on Aug. 27, 2018, 48 Kb is herein incorporated by reference.

SEQ ID NOS: 1 and 2 show the full-length gene sequence encoding the α-amylase of G. *stearothermophilus*, and the corresponding amino acid sequence, respectively.

SEQ ID NOS: 3, 5, 7, 9, and 11 show the nucleotide coding sequence of α-amylase variants.

SEQ ID NOS: 4, 6, 8, 10 and 12 show the amino acid sequence of α-amylase variants.

SEQ ID NO: 13 shows a synthetic promoter sequence.

SEQ ID NO: 14 shows a synthetic terminator sequence.

SEQ ID NO: 15 shows a natural signal sequence.

SEQ ID NOS: 16-17 are forward and reverse primer sequences, respectively, used to amplify the upstream sequence of the Apr gene.

SEQ ID NOS: 18-19 are forward and reverse primer sequences, respectively, used to amplify the downstream sequence of the Apr gene.

SEQ ID NOS: 20-21 are forward and reverse primer sequences, respectively, used to amplify the upstream sequence of the Blase gene.

SEQ ID NOS: 22-23 are forward and reverse primer sequences, respectively, used to amplify the downstream sequence of the Blase gene.

DETAILED DESCRIPTION OF THE INVENTION

Unless otherwise specified, all technical and scientific terms used herein have the same meanings as commonly understood by skilled persons. In this application, certain terms have the same meanings as the specification describes. It must be noted that as used herein and in the appended claims, the singular forms "a", "an", and "the" may include plural forms unless the context clearly dictates otherwise.

In the present invention, the term "α-amylase" refers to an enzyme capable of hydrolyzing an α-1,4 glycosidic bond of a polysaccharide. For example, the α-amylase can hydrolyze starch to dextrin.

In the present invention, the term "parental α-amylase" refers to a natural α-amylase. The natural α-amylase is a bacterial α-amylase and its source includes, but is not limited to, *Bacillus subtilis*, *B. licheniformis*, *B. amyloliquefaciens*, *G. stearothermophilus* and *Bacillus cereus*.

According to a preferred embodiment of the present invention, the natural α-amylase is derived from a *Bacillus* strain, especially *B. licheniformis* and *G. stearothermophilus*. The full-length encoding sequence of the α-amylase of *G. stearothermophilus* is set forth in SEQ ID NO: 1, and the corresponding amino acid sequence is set forth in SEQ ID NO: 2.

In the present invention, the term "α-amylase variant" refers to a non-naturally occurring α-amylase obtained by mutation or deletion of one or several amino acid residues in the amino acid sequence of the parental α-amylase, while still retaining the ability of the parental α-amylase to hydrolyze an α-1,4 glycosidic bond.

In the present invention, the term "liquefaction" generally refers to the process of breaking down carbohydrates into small molecule polysaccharides. When an α-amylase or α-amylase variant is added, "liquefaction" specifically refers to hydrolyzing the α-1,4 glycosidic bond of the carbohydrate.

In the present invention, the term "α-1,4 glycosidic bond" refers to a bond linking C1 of the former glucose with C4 of the latter glucose, that is, an α-1,4 glycosidic bond.

The present invention relates to an "α-amylase variant" obtained by sequence modification of a parental α-amylase. The parental α-amylase is a natural α-amylase, particularly a natural α-amylase derived from bacteria. According to an embodiment of the present invention, an α-amylase variant is obtained by the mutation or deletion of one or several amino acid residues in the amino acid sequence of the parental α-amylase.

The present invention includes a series of α-amylase variants. According to an embodiment of the present invention, the homology of the amino acid sequences of the series of α-amylase variants is at least 95%, even 95%, 96%, 97%, 98%, 99% or 100%, respectively.

As an illustrative and non-limiting example of the invention, the α-amylase variant is obtained by any one of the following:

(1) deleting the $1^{st}$ to $5^{th}$ amino acid residues from the N-terminus and replacing with VN, and deleting the $1^{st}$ to $27^{th}$ amino acid residues from the C-terminus of the parental α-amylase of *G. stearothermophilus*, with an amino acid sequence as set forth in SEQ ID NO: 4.

(2) deleting the $1^{st}$ to $5^{th}$ amino acid residues from the N-terminus and replacing with ANLN, deleting the $180^{th}$ and $181^{st}$ amino acid residues from the N-terminus, and deleting the $1^{st}$ to $27^{th}$ amino acid residues from the C-terminus of the parental α-amylase of *G. stearothermophilus*, with an amino acid sequence as set forth in SEQ ID NO: 6.

(3) deleting the $1^{st}$ to $5^{th}$ amino acid residues from the N-terminus and replacing with ANLN, deleting the $180^{th}$ and $181^{st}$ amino acid residues from the N-terminus, and deleting the $1^{st}$ to $29^{th}$ amino acid residues from the C-terminus of the parental α-amylase of *G. stearothermophilus*, with an amino acid sequence as set forth in SEQ ID NO: 8.

(4) deleting the $1^{st}$ to $5^{th}$ amino acid residues from the N-terminus and replacing with ANLN, deleting the $180^{th}$ and $181^{st}$ amino acid residues from the N-terminus, and deleting the $1^{st}$ to $32^{nd}$ amino acid residues from the C-terminus of the parental α-amylase of *G. stearothermophilus*, with an amino acid sequence as set forth in SEQ ID NO: 10.

(5) deleting the $1^{st}$ to $5^{th}$ amino acid residues from the N-terminus and replacing with ANLN, deleting the $180^{th}$ and $181^{st}$ amino acid residues from the N-terminus, deleting the $1^{st}$ to $27^{th}$ amino acid residues from the C-terminus, and adding three amino acid residues of FAN at the C-terminus of the parental α-amylase of *G. stearothermophilus*, with an amino acid sequence as set forth in SEQ ID NO: 12.

The amino acid sequence of the α-amylase variant is any one selected from the group consisting of SEQ ID NO: 6, SEQ ID NO: 8, SEQ ID NO: 10 and SEQ ID NO: 12.

The α-amylase variant of the present invention retains the ability to hydrolyze the α-1,4 glycosidic bond. In addition, the performance of these α-amylases meets the requirements of industrial production, such as the improvement of liquefaction efficiency, and the stable catalytic activity at an acidic pH or a high temperature.

According to an embodiment of the present invention, the α-amylase variant is stable in catalytic activity at an acidic condition of pH 5.0 or at a temperature of 100° C. or above (especially at a temperature between 100° C. and 110° C.). The improved properties of the α-amylase variant are more amenable to the liquefaction reactions in the starch industry, because the liquefaction process in the starch industry is often carried out at conditions of a low pH and a high temperature.

All α-amylase variants of the present invention can be used in the liquefaction reaction. In a preferred embodiment, the α-amylase variant is derived from a parental α-amylase, in particular a parental α-amylase derived from *G. stearothermophilus*. In a particularly preferred embodiment, the amino acid sequence of the α-amylase variant is set forth in any one of SEQ ID NO: 4, SEQ ID NO: 6, SEQ ID NO: 8, SEQ ID NO: 10 and SEQ ID NO: 12.

According to the present invention, any carbohydrate containing α-1,4 glycosidic bond can be used in the liquefaction reaction. The carbohydrates containing one or more α-1,4 glycosidic bonds include but are not limited to starch, amylopectin, amylose, and dextran.

Many carbohydrates contain an α-1,6-glycosidic bond and an α-1,4-glycosidic bond, such as amylopectin. The term "α-1,4-glycosidic bond" refers to a bond linking C1 of the former glucose with C4 of the latter glucose, that is, an α-1,4 glycosidic bond. Therefore, the α-amylase variant of the present invention can be used in conjunction with a pullulanase capable of hydrolyzing an α-1,6 glycosidic bond during saccharification. The enzymes capable of hydrolyzing an α-1,4 glycosidic bond include, but are not limited to, α-amylases. In a preferred embodiment of the present invention, the enzyme that catalyzes the hydrolysis of an α-1,4 glycosidic bond is an α-amylase.

Therefore, according to an embodiment of the present invention, a method for further catalyzing the saccharification reaction to increase the efficiency is to use pullulanase in combination. In the present invention, the term "pullulanase" refers to a hydrolase capable of hydrolyzing an α-1,6 glycosidic bond.

The use of the α-amylase of the present invention in combination with pullulanase in the saccharification of starch can increase the purities of glucose and maltose. In addition, the use of the aforementioned complex enzyme in the saccharification reaction can effectively reduce the substrate concentration, increase the conversion efficiency, and can also have a higher catalytic activity at an acidic pH or a higher temperature, and can be more adapted to industrial conditions for hydrolyzing starch.

The present invention provides a method in which an α-amylase variant can hydrolyze an α-1,4 glycosidic bond for saccharification under any temperature and pH conditions suitable for industrial production. According to the present invention, the liquefaction reaction can be carried out at a high temperature of 80° C. to 110° C., such as 80° C., 90° C., 100° C., 105° C., and 110° C. The saccharification reaction can also be carried out under an acidic pH condition of pH 5.0 to pH 5.5, such as pH 5.0, 5.1, 5.2, 5.3, 5.4, and 5.5.

According to an embodiment of the present invention, the catalytic activity is stable in the liquefaction reaction catalyzed by an α-amylase variant under conditions of an acidic pH and a temperature of 100° C. or above.

In another aspect, the expression vector of the present invention comprises a synthetic nucleotide sequence encoding an α-amylase variant, and a recombinant host cell comprises the above expression vector. The expression vector may comprise a series of synthetic nucleotide sequences encoding different α-amylase variants. The expression vector can be integrated into the genome of the host cell. For example, the expression vector may comprise the synthetic nucleotide sequence SEQ ID NO: 3, SEQ ID NO: 5, SEQ ID NO: 7, SEQ ID NO: 9 and SEQ ID NO: 11.

The expression vector of the present invention preferably comprises a natural or synthetic promoter sequence, a natural or synthetic ribosome binding site, and a natural or synthetic terminator sequence. These genetic elements together with the encoding sequence of the synthetic α-amylase variant constitute an expression cassette, which constitutes an expression vector together with a vector backbone. For example, the expression vector comprises an expression cassette which includes the following elements: a promoter sequence, a synthetic ribosome binding site, a synthetic nucleotide sequence encoding an α-amylase variant of the present invention and a terminator sequence. A signal sequence is capable of directing the secretion of the α-amylase variant, and the introduction of the signal sequence into the expression vector or expression cassette, especially the introduction of the signal sequence upstream of the start codon is more advantageous for the secretion of the α-amylase variant.

According to a preferred embodiment of the present invention, the expression vector is suitably expressed in bacteria, in particular a *Bacillus* strain, and more preferably expressed in *B. licheniformis*. In a particularly preferred embodiment, the expression vector can be integrated into the genome of *Bacillus*, in particular the genome of *B. licheniformis*. The expression vector for a host cell that can be used for integration of polynucleotide sequences in chromosome and a method for constructing such an expression vector are well-known common skills in the field of contemporary biology.

According to an embodiment of the present invention, the recombinant host cell may be genetically engineered to comprise one or more nucleic acid sequences encoding α-amylase variant. Any technique can be used to genetically engineer a host cell to comprise one or more synthetic nucleic acid sequences encoding the α-amylase variant of the present invention, e.g., chromosomal integration. A vector containing a temperature-sensitive origin and a resistance selection marker can be used for the integration step. The vector is integrated with a specific region of the genome through the Campbell mechanism, and a recombinant strain is obtained through resistance screening. The resistance screening marker of the recombinant strain is removed by homologous recombination during the subsequent cultivation.

According to an embodiment of the present invention, the recombinant host cell has been engineered to inactivate some endogenous proteins. The endogenous proteins that can be inactivated include, but are not limited to, extracellular proteases. Some endogenous proteins are inactivated either before or after the recombinant host cell is transformed with a nucleic acid sequence containing an α-amylase variant expressing gene. A more suitable method is to inactivate the exogenous secreted protease of the host bacterium before transferring the vector of the α-amylase variant expressing gene.

First, *B. licheniformis* has been modified to inactivate some exogenous protease genes. In particular, some extracellular proteases, such as subtilisin (AprE), glutamic acid-specific protease (Blase) can be inactivated in the *B. licheniformis* strain. The genetic engineering makes the *B. licheniformis* strain more suitable for the expression and secretion of an α-amylase variant.

The present invention provides a method for producing an α-amylase variant. According to an embodiment of the present invention, the method comprises culturing a recombinant host cell containing a nucleotide sequence encoding an α-amylase variant under conditions suitable for the expression of an α-amylase variant and obtaining the α-amylase variant from the recombinant host cell or its supernatant.

All recombinant host cells of the present invention are capable of producing α-amylase variants. The recombinant host cell comprises at least one copy of a nucleotide sequence encoding an α-amylase variant. The nucleotide sequences encoding an α-amylase variant is capable of expressing the α-amylase variant under suitable conditions. The α-amylase variant secreted from the recombinant host cell can be collected from the recombinant cell or supernatant. The collection method includes but is not limited to filtration, centrifugation, and the like.

According to an embodiment of the present invention, an α-amylase variant can be produced in large amount by fermentation of genetically engineered *B. licheniformis*. The nucleotide sequence encoding the α-amylase variant is introduced into *B. licheniformis* by genetic engineering. More preferably, *B. licheniformis* of the present invention has been modified to remove the resistance screening gene and is environmentally friendly, and the produced α-amylase variant is more suitable for use in the food industry.

The following examples of the present invention further illustrate the essence of the present invention. It should be understood that the following examples do not limit the present invention, and the scopes of the present invention are determined by the appended claims.

EXAMPLES

Example 1

Construction of pYF-tsDE Plasmid pYF-tsDE (FIG. 1) was a thermosensitive *E.coli/B. licheniformis* shuttle plasmid. The plasmid comprised a temperature-sensitive replication origin (being active at 30° C.) and an erythromycin resistance gene (ErmC), the resistance of which was 300 μg/ml in *E. coli*, and 5 μg/ml in *B. licheniformis*. At 37° C., the replication origin on the plasmid was inactivated and the plasmid was integrated into the specified site of the host genome and screened with ErmC.

Figure 2:
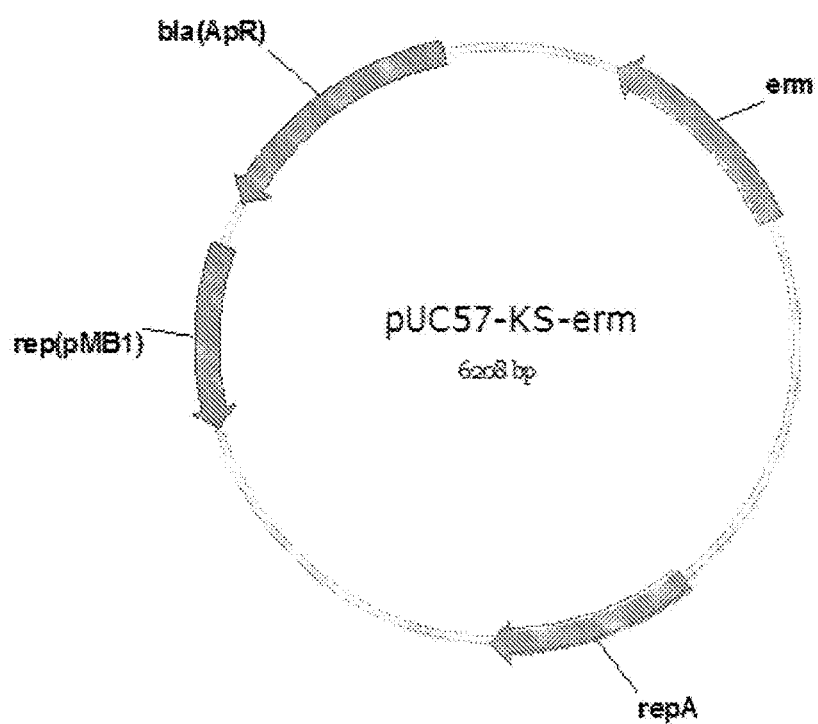
FIG. 2 is a schematic diagram of a pUC57-KS-erm vector from which the pYF-tsDE vector of the present invention can be obtained.

The pYF-tsDE plasmid was constructed by digesting the plasmid pUC57-KS-erm (synthesized by Genscript with commission, and the sequence was shown in CN 104073458A, FIG. 2) with BglII, recovering, purifying a 3.8 kbp fragment and self-ligating with T4 ligase (New England Biolabs), and the cloned plasmid was pYF-tsDE. Transformants were propagated in *E. coli* TOP10 and served as the backbone for all of the following gene manipulations.

Example 2

Construction of a Protease Deficient *B. licheniformis* Strain

Genetically engineered strains that are host cells for recombinant enzyme products have been reported in the literature (Widner et al., Journal of Industrial Microbiology & Biotechnology, 25, 204-212, 2000). These recombinant host cells typically contain one or more nucleic acid structures coding a target sequence for expression of an enzyme. In the present invention, *B. licheniformis* is used as a genetically manipulated recipient bacterium. The transformation of *Bacillus* can now be achieved through very mature means such as competent cell transformation, electrotransformation and protoplast transformation (Young et al., J Bacteriology, 81, 823-829, 1961; Shigekawa et al., Biotechniques, 6, 742-751, 1988; Chang et al., Molecular General Genetics, 168, 111-115, 1979).

In the present invention, a single expression cassette for α-amylase variant comprised a natural or synthetic promoter sequence, a signal peptide sequence screened from *Bacillus*, a synthetic ribosome binding site, and an α-amylase variant coding gene from *G. stearothermophilus*, and a transcription terminator. Such a design would greatly enhance the level of gene expression in the host strain and the secretion amount of the α-amylase variant. Replacing a specific site on the genome of the *B. licheniformis* cell with the α-amylase variant coding gene was achieved by plasmid-mediated single cross-homologous recombination.

In *B. licheniformis*, the activities of extracellular proteases are detrimental to the secretion of heterologous enzymes. Two major extracellular proteases have been identified: subtilisin (AprE) and glutamic acid-specific protease (Blase). Most of the extracellular protease activities in *B. licheniformis* originate from these two proteases.

In the present invention, in order to obtain the structural integrity of the α-amylase variant gene, the above two genes were inactivated, and the continuous cross single Campbell type mechanism was adopted. The specific operation was as follows:

2.1 pYF-tsDE was Digested by BglII and Treated with CIP to Inhibit Self-Ligation;

2.2 Gene Knockout (1) In order to obtain each gene deletion fragment, a homologous sequence of approximately 500 bp was respectively amplified from each side of the gene to be deleted by PCR using the genomic DNA of *B. licheniformis* (CICC 22794, purchased from the China Center of Industrial Culture Collection) as a template. The monoclonal *B. licheniformis* was pre-denatured at 98° C. for 5 minutes and could be used directly as a genomic DNA template in a PCR reaction.

The primers used for the PCR reaction were synthesized by Genscript. The primer sequences were as follows:

The primers for amplifying the upstream sequence of the Apr gene were:

```
lichApr_F1
                                     (SEQ ID NO: 16)
TTATTGAGCGGCAGCTTCGACATTGATCAGACCTT lichApr_R1
                                     (SEQ ID NO: 17)
CCTTACGGCATTCCTCTCAACAGCGGATCTTCAG
```

The primers for amplifying the downstream sequence of the Apr gene were:

```
lichApr_F2
                                     (SEQ ID NO: 18)
CCTGAAGATCCGCTGTTGAGAGGAATGCCGTAAGG lichApr_R2
                                     (SEQ ID NO: 19)
ATGATGAGGAAAAAGAGTTTTTGGCTTGGGATGCTGAC
```

The primers for amplifying the upstream sequence of the Blase gene were:

```
blalich_F1
                                     (SEQ ID NO: 20)
TTATTGTGCGCTGTTTTTCCAGTTGGTCAAATTGTCG blalich_cR1
                                     (SEQ ID NO: 21)
CGGACAAGGGTCACCAACGGGACAACTGTTACCATC
```

The primers for amplifying the downstream sequence of the Blase gene were:

```
blalich_cF2
                                     (SEQ ID NO: 22)
GATGGTAACAGTTGTCCCGTTGGTGACCCTTGTCC blalich_R2
                                     (SEQ ID NO: 23)
CGGCGTTGGTTAGTAAAAAGAGTGTTAAACGAGGTTTGAT
```

The PCR amplification system was 50 μl and the reaction procedure was as follows:

(1) monoclonal *B. licheniformis* 14580 pre-denatured at 98° C. for 8 minutes;
(2) 96° C., 15 seconds;
(3) 58° C., 15 seconds;
(4) 72° C., 30 seconds; steps 2-4 repeated for 25-30 times;
(5) Final extension at 72° C., 2 minutes.

The PCR product was detected by 0.8% agarose gel electrophoresis and purified using an Axygen kit.

2.3 Amplification of a Target Gene with an Internal Deletion of Approximately 400-500 bp in the Sequence by Overlap Extension PCR Method The internal gene deletion fragment was obtained using overlap extension PCR (SOE). The specific operation was as follows:

(1) The upstream and downstream PCR fragments of each gene in 2.2 were recovered and purified;

(2) Using the upstream and downstream homologous fragments of each gene of interest in 1:1 molar ration as template, PCR amplification was performed using primers XX-CZ-F1 and XX-CZ-R2 ("XX" for Apr or Blase) to obtain the AprE gene or Blase gene with internal fragments deleted.

The fragments were then recombined into the BglII-linearized pYF-tsDE vector using a Clone-EZ Cloning Kit (provided by Genscript) and the resulting recombinant plasmids were named: pYF-tsDE-Apr and pYF-tsDE-Blase. These recombinant plasmids were temperature-sensitive plasmids, and the Apr gene or Blase gene contained therein lacks an internal sequence of about 400-500 bp with respect to the intact gene, respectively.

Replacement of different alleles can be achieved by homologous recombination.

The method can be referred to CN102124112A, and other well-known methods of homologous recombination in the art can also be used.

2.4 Plasmid Transformation

The method for transforming a knockout plasmid into competent cells of *B. licheniformis*, and the screening process used in the experiment were as follows:

(1) The thermosensitive plasmid pYF-tsDE-Apr or pYF-tsDE-Blase was used to transform *B. licheniformis* (CICC 22794, purchased from China Center of Industrial Culture Collection) competent cells;

(2) Positive clone strains were screened with erythromycin (5 μg/ml) resistance on LB (10 g of peptone, 5 g of yeast extract, and 10 g of sodium chloride per liter) medium at 30° C.;

(2) The positive clone strains were then transferred to condition of 37° C. for incubation, allowing the temperature-sensitive plasmid to be fused to the host genome. In order to replace the gene at the preset position, several clones were selected and inoculated in 2×YT medium for 24 hours, and then subcultured once. The whole process was subcultured for 4-5 times (generally 5-7 days).

(3) Erythromycin-sensitive *Bacillus subtilis* cells were screened for PCR identification. The transparent hydrolysis circle could be observed with a 1% skim milk LB plate at the same time. The knockout strain should show a significantly reduced hydrolysis circle.

PCR primers used in the identification:

```
AprE: Apr-seqF1/Apr-seqR3

Blase: Blase-seqF1/Blase-seqR3

Apr-seqF1: GCCAGGTTGAAGCGGTCTATTCAT
```

-continued

Apr-seqR3: TACGGCCATCCGACCATAATGGAAC

Blase-seqF1: GAAGAGCCGGTCACAATTGC

Blase-seqR3: GGCCGTTAGATGTGACAGCC

Example 3

Integration and Construction of α-Amylase Variant Strain 3.1 Construction of Amylase Expression Cassette The integration plasmid was constructed using the same method as the pYF-tsDE plasmid described above. In order to integrate the expression cassette into the designed AmyE site on the genome, a homologous region of about 800 bp was respectively designed upstream and downstream of the AmyE site on the genome and ligated on both sides of an α-amylase variant expression cassette. At the same time, a number of completely naturally selected bacterial chromosomal DNA fragments and functional synthetic sequences were assembled, which were necessary for controlling the expression of the α-amylase variant gene.

Figure 3:
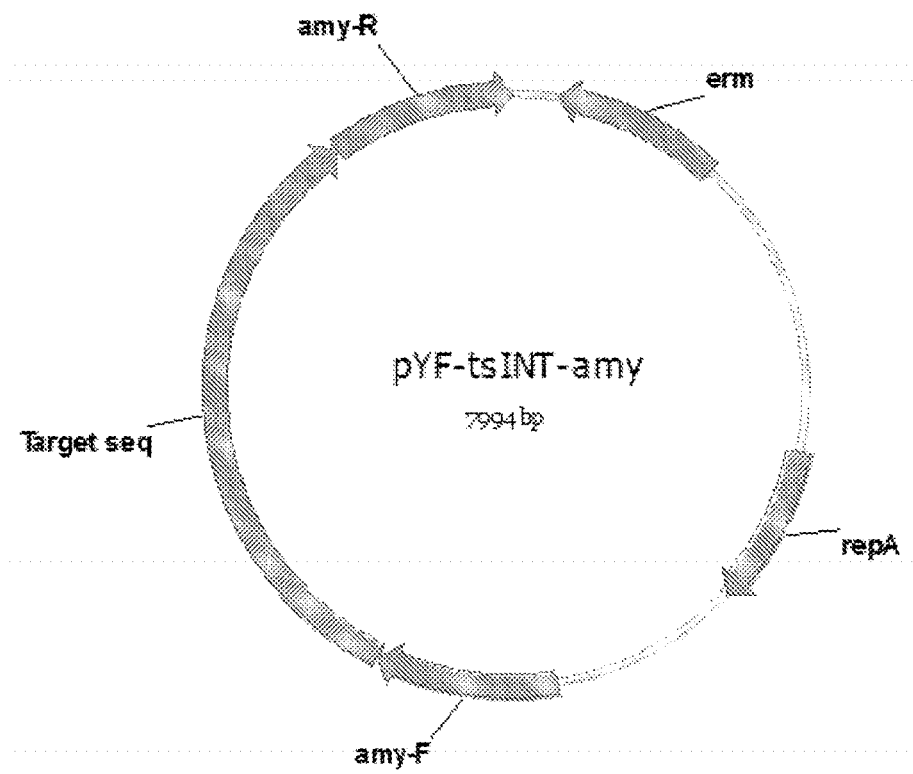
FIG. 3 is a schematic diagram of a pYF-tsINT-amy vector.

A typical amylase expression cassette comprised the following components. A typical α-amylase variant expression cassette comprised the following elements: a natural or synthetic promoter sequence (SEQ ID NO: 13), a synthetic ribosome binding site aaaggagg, an α-amylase variant coding gene derived from G. stearothermophilus (SEQ ID NO: 3, SEQ ID NO: 5, SEQ ID NO: 7, SEQ ID NO: 9 or SEQ ID NO: 11, respectively) and a synthetic terminator sequence (SEQ ID NO: 14). A strong natural signal sequence (SEQ ID NO: 15) screened from Bacillus subtilis was inserted upstream of the promoter of the α-amylase variant coding gene to enhance the secretion efficiency of the expressed enzyme. The complete α-amylase variant expression cassette was inserted into the BglII site in the linearized pYF-tsDE using a Clone-EZ Cloning Kit (Genscript). The resulting temperature-sensitive integration plasmid was named pYF-tsINT-amy (FIG. 3). The synthesis of the above sequence was performed by Genscript, and the above sequences were sequentially tandemly connected to obtain an α-amylase enzyme expression cassette. The signal peptide sequence in this cassette was screened from Bacillus subtilis and could effectively increase the secretion of α-amylase.

3.2 Plasmid Transformation

The entire α-amylase expression cassette (including homologous segments upstream and downstream of the amyE gene) was circularized using a recombinant technique to cyclize the BglII-linearized pYF-tsDE plasmid (recombination kit provided by Genscript), and the constructed thermosensitive plasmid was named as pYF-tsINT-amy. The plasmid was used for transformation into Bacillus licheniformis with deletion of the AprE and Blase protease genes (CICC 22794, purchased from China Center of Industrial Culture Collection), and the α-amylase variant expression cassette without resistance marker was going to replace AmyE. Using the method described above, a strain in which the α-amylase variant coding gene was successfully integrated into the chromosome of B. licheniformis produced a transparent circle on the blue starch plate, and PCR further confirmed that the expression cassette was integrated in the AmyE site of the recipient strain.

The B. licheniformis engineered strain that produced an α-amylase variant was stored at −80° C.

Example 4

Shake Flask Fermentation of α-Amylase Variant Production

An activated bacterial monoclone (containing the α-amylase variant expression cassette) was inoculated into 20 ml medium (containing maltose syrup 4.0%, peptone 2.0%, yeast powder 0.1%, $KH_2PO_4$ 0.6% and corresponding antibiotics) to log phase. 1.2 ml of the culture solution was inoculated into 30 ml medium (containing maltose syrup 12.0%, peptone 1.0%, yeast powder 1%, $KH_2PO_4$ 0.2%, and $MnCl_2$ 0.003%), and cultured on a reciprocating shaker at 120 rpm for 3 days. Samples were taken at 24 hours, 48 hours and 72 hours, respectively, and centrifuged at 1000 rpm for 1 minute. The supernatant was stored and analyzed by SDS-PAGE. The α-amylase variant had a molecular weight of about 53 kD.

The α-amylase variant activity was measured as described in Example 6.

Example 5

Step-Feeding Fermentation Process for α-Amylase Variant

The genetically engineered B. licheniformis strain cryo-preserved at −80° C. obtained in Example 3 was streaked on an agar slant, and cultured overnight at 37° C. The agar slant formula was as follows: peptone 1%, yeast extract 0.5%, NaCl 1%, and agar powder 2%.

First, several fresh clones were selected and cultured in a seed shake flask containing 50 ml of culture medium at 37° C. for 16 hours. Seed shake flask formula: maltose syrup 4.0%, peptone 2.0%, yeast extract 0.1%, and $KH_2PO_4$ 0.6%. After 16 hours, all the seed broths were transferred to a 7 L stainless steel fermenter containing 4 L of culture medium and the fermentation was continued for 12 hours at agitation speed of 350 rpm and an aeration rate of 650 L/H. Fermenter formula: malt syrup 6.0%, peptone 1.0%, yeast extract 1%, $KH_2PO_4$ 0.2%, and $MnCl_2$ 0.003%. The fermentation pH was then controlled at about 5.7±0.2 with 5% phosphoric acid and the fermenter was continuously fed at a rate of 1 L/18 hrs in the first 18 hours and at a rate of 0.5 L/18 hrs for the next 110 hours. The feed formula was as follows: maltose syrup 48%, peptone 6%, and yeast extract 8%. The entire fermentation process lasted 140-150 hours. All media in the fermenter were collected and centrifuged at 4° C., 1010 krpm for 30 minutes. The supernatant after centrifugation was used for α-amylase variant enzymatic activity analysis.

Example 6

Amylase Activity Assay

The amylase activity assay was performed using Bestzyme amylase unit (BAU). One BAU is defined as the amount of enzyme required to liquefy 1 mg of soluble starch in 1 minute at pH 6.0 and 70° C.

Briefly, the enzyme activity was determined as follows: 20 ml of 20 g/L soluble starch solution was mixed with 5 ml of phosphate buffer pH 6.0, preheated at 70° C. for 8 min, then 1.0 ml of diluted enzyme solution was added, and the reaction was accurately performed for 5 minutes. 1 ml of the reaction solution was added to a test tube containing in advance 0.5 ml of 0.1 mol/L hydrochloric acid solution and 5 ml of dilute iodine solution, and shaken well. With 0.5 ml 0.1 mol/L hydrochloric acid solution and 5 ml dilute iodine solution as a blank, the absorbance value was quickly measured at a wavelength of 660 nm, and the enzymatic activity of the test sample was obtained by checking the table according to the absorbance.

Example 7

Application of Amylase

All of the following results were based on the sequence of the α-amylase variant SEQ ID NO: 8.

Unless otherwise stated, 1 BAU: the amylase activity assay was performed using Bestzyme amylase unit (BAU). One BAU is defined as the amount of enzyme required to liquefy 1 mg of soluble starch in 1 minute at pH 6.0 and 70° C.

tDS: dry matter per ton

Figure 4:
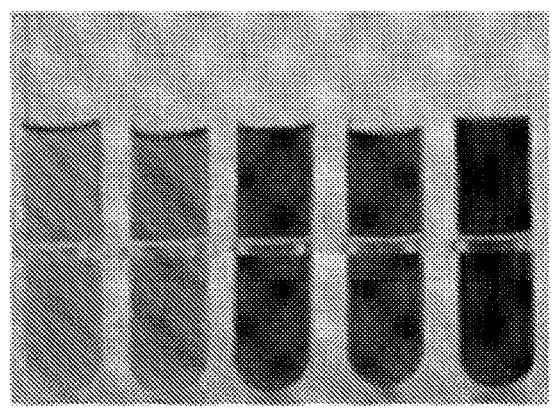
FIG. 4 shows the protein flocculation and viscosity.

The amylase expressed and isolated from the *B. licheniformis* cells was first subjected to a first round of liquefaction test using corn starch. Test conditions: 18 Baume degrees (° Bé), well-mixed, pH adjusted to 5.2 with hydrochloric acid. 0.22 kg/tDS of amylase was added, with a jetting temperature of 100° C., 105° C., 108° C., 110° C., and 115° C., respectively, maintained for 5 to 8 minutes followed by flashing and then maintained at 95° C. for 120 minutes. After liquefaction, the DE and iodine tests were performed, and the protein flocculation and viscosity were observed. The results are shown in Table 1 and FIG. 4.

TABLE 1

Comparison of amylase liquefactions at different jetting temperatures

| Temperature (° C.) | DE (%) |
|---|---|
| 100 | 17.64 |
| 105 | 14.91 |
| 108 | 10.62 |
| 110 | 10.21 |
| 115 | 3.06 |

The results showed that, at different jetting temperatures, the liquefaction at 100° C. was overdone; the liquefaction at 105° C. was appropriate and the protein flocculation was good; the liquefaction at 108° C. and 110° C. was still good and the protein flocculation was normal, indicating that the α-amylase variant had good heat resistance, while the liquefaction at 115° C. was poor, indicating that the α-amylase variant could not tolerate the high temperature of 115° C.

Figure 5:
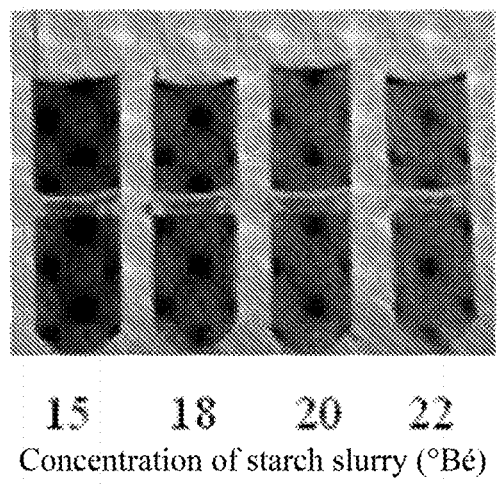
FIG. 5 is a graph showing the results of liquefaction experiments under different starch slurry concentrations.

Secondly, we tested the resistance of the amylase to high substrate concentration by liquefaction experiments with different starch slurry concentrations. The liquefaction conditions were the same as those described above, and the jetting temperature was 108° C. The results are shown in Table 2 and FIG. 5.

TABLE 2

Comparison of amylase liquefactions at different concentrations of starch slurry

| Baume degree (° Bé) | DE (%) |
|---|---|
| 15 | 8.58 |
| 18 | 10.73 |
| 20 | 12.10 |
| 22 | 14.29 |

As shown in Table 2, at different starch slurry concentrations, the α-amylase variant was still able to normally liquefy when the concentration of the starch slurry was as high as 22° C.é, indicating that the α-amylase variant of the present invention could be used for thick slurry liquefaction, thereby effectively saving factory costs.

Figure 6:
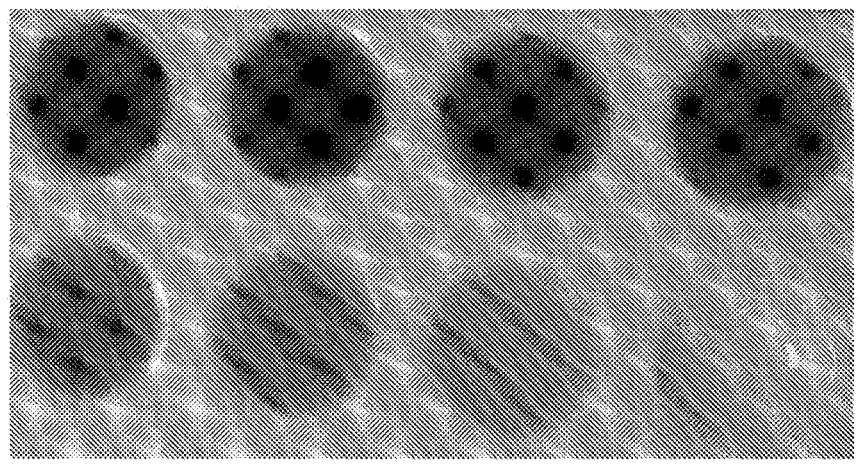
FIG. 6 shows the results of acid resistance experiments of the α-amylase variants.

Then, we measured the acid resistance of the amylase variant and performed liquefaction with different amounts of enzyme added. The liquefaction reaction conditions were as described above, the pH was 5.0, and the amount of enzyme added was 0.05, 0.1, 0.15, 0.2, 0.22, 0.25, and 0.3 kg/tDS, respectively. The results are shown in Table 3 and FIG. 6.

TABLE 3

Comparison of amylase liquefactions with different amounts of enzyme added at pH 5.0

| Amount of enzyme added (kg/tDS) | DE (%) |
|---|---|
| 0.05 | 3.41 |
| 0.10 | 6.18 |
| 0.15 | 8.04 |
| 0.20 | 8.12 |
| 0.22 | 9.81 |
| 0.25 | 10.41 |
| 0.30 | 11.77 |

As shown in Table 3, under the conditions of low pH with addition of 0.15 to 0.3 kg/tDS, the α-amylase variant was still able to normally liquefy, indicating that the α-amylase variant was highly tolerant to low pH, and at the same time, under condition of a small amount of enzyme added of 0.15 kg/tDS, the α-amylase variant of the present invention was still able to normally liquefy, which could effectively reduce the cost for enzyme used in factories.

In addition, we performed a test for the effect of α-amylase variant on saccharification and compared it with a liquefaction solution liquefied with Liquozyme Supra (purchased from Novozymes). Test conditions: 32% dry matter (DS), well-mixed, pH adjusted to 4.3 with hydrochloric acid. 0.45 kg/tDS complex glucoamylase was added and the reactions of 200 ml were conducted at 60° C. for 24 and 48 hours, respectively. Samples were filtered by 0.22 μm membrane and inactivated at 100° C. for HPLC analysis. The results are shown in Table 4.

TABLE 4

Effect of the α-amylase variant on saccharification

| Amylase | Glucose % | |
|---|---|---|
| | 24 hrs | 48 hrs |
| α-amylase variant | 95.11 | 96.4 |
| Liquozyme Supra | 95.55 | 96.38 |

As shown in Table 4, the liquefaction solution of the α-amylase variant and the liquefaction solution of Liquozyme Supra had the same saccharification effect, indicating that the α-amylase variant could be applied to the starch sugar industry.

Finally, because α-amylase has important applications in the alcohol industry, we have also tested the liquefaction effect of this α-amylase variant on alcohol production. Corn flour (40 mesh) with a ratio of feed to water of 1:2.5 was prepared, the pH was adjusted to 5.8 with hydrochloric acid, and 0.145 kg/t DS of the α-amylase variant was added. The solution was liquefied at 95° C. for 120 min. After the reaction was completed, the DE and the viscosity of the sample were measured, and a comparative test with Liquozyme SC (available from Novozymes) was also conducted at the same time. The results are shown in Table 5.

TABLE 5

Comparison of application of α-amylase
variant in corn alcohol liquefaction

| Amylase | DE (%) | viscosity (mPas) |
|---|---|---|
| α-amylase variant | 10.02 | 11650 |
| Liquozyme SC | 10.05 | 11710 |

As shown in Table 5, the α-amylase variant could achieve the same application effect as Liquzoyme SC, indicating that it could be applied to the corn alcohol industry.

In summary, according to the experimental results in the present invention, the series of α-amylase variants had better heat resistance and pH tolerance, and could be applied to the liquefaction of high-strength starch slurry, and thus could be applied to the starch sugar industry and the alcohol industry.

The examples of the present invention are inseparable from the teachings of the present invention in addition to the technical means in the art. Therefore, the invention is not limited to the specific examples disclosed, but also to additional modifications within the spirit and scope of the invention, as described in details in the appended claims.

The invention claimed is:

1. An α-amylase variant, comprising:
a *G. stearothermophilus* parental α-amylase amino acid sequence set forth in SEQ ID NO: 2 comprising an N-terminus and a C-terminus, which is mutated and retains the ability to hydrolyze an α-1,4 glycosidic bond;
wherein SEQ ID NO: 2 is mutated to comprise:
   (1) deletion of amino acid residues 1 to 5 from the N-terminus and replacing deleted amino acid residues 1 to 5 with amino acid residues VN or ANLN;
   (2) deletion of amino acid residues 180 and 181 from the N-terminus;
   (3) deletion of amino acid residues 1 to 5 from the N-terminus and replacing deleted amino acid residues 1 to 5 with amino acid residues VN or ANLN, and deletion of 27 to 32 amino acid residues from the C-terminus;
   (4) deletion of 27 to 32 amino acid residues from the C-terminus, and deletion of amino acid residues 180 and 181 from the N-terminus; or
   (5) deletion of amino acid residues 1 to 5 from the N-terminus and replacing deleted amino acid residues 1 to 5 with amino acid residues VN or ANLN, deletion of 27 to 32 amino acid residues from the C-terminus, and deletion of amino acid residues 180 and 181 from the N-terminus.

2. The α-amylase variant according to claim 1, wherein the α-amylase variant further comprises amino acid residues FAN added to the C-terminus.

3. The α-amylase variant according to claim 1, wherein the amino acid sequence of the α-amylase variant is any one selected from the group consisting of SEQ ID NO: 4, SEQ ID NO: 6, SEQ ID NO: 8, SEQ ID NO: 10 and SEQ ID NO: 12.

4. The α-amylase variant according to claim 3, wherein the nucleotide coding sequence of the α-amylase variant is any one selected from the group consisting of SEQ ID NO: 3, SEQ ID NO: 5, SEQ ID NO: 7, SEQ ID NO: 9 and SEQ ID NO: 11.

5. The α-amylase variant of claim 1, wherein the *G. stearothermophilus* parental α-amylase amino acid sequence is encoded by the nucleic acid sequence of SEQ ID NO: 1.

\* \* \* \* \*

SEQUENCE LISTING

<160> NUMBER OF SEQ ID NOS: 23

<210> SEQ ID NO 1
<211> LENGTH: 1542
<212> TYPE: DNA
<213> ORGANISM: Geobacillus stearothermophilus

<400> SEQUENCE: 1

```
gccgcaccgt ttaacggcac catgatgcag tattttgaat ggtacttgcc ggatgatggc      60
acgttatgga ccaaagtggc caatgaagcc aacaacttat ccagccttgg catcaccgct     120
ctttggctgc cgcccgctta caaggaaca agccgcagcg acgtagggta cggagtatac     180
gacttgtatg acctcggcga attcaatcaa aaagggaccg tccgcacaaa atacggaaca     240
aaagctcaat atcttcaagc cattcaagcc gcccacgccg ctggaatgca agtgtacgcc     300
gatgtcgtgt tcgaccataa aggcggcgct gacggcacgg aatgggtgga cgccgtcgaa     360
gtcaatccgt ccgaccgcaa ccaagaaatc tcgggcacct atcaaatcca agcatggacg     420
aaatttgatt ttcccgggcg gggcaacacc tactccagct ttaagtggcg ctggtaccat     480
tttgacggcg ttgattggga cgaaagccga aaattgagcc gcatttacaa attccgcggc     540
aaagcgtggg attgggaagt agacacggaa tttggaaact atgactactt aatgtatgcc     600
gaccttgata tggatcatcc cgaagtcgtg accgagctga aaaactgggg gaaatggtat     660
gtcaacacaa cgaacattga tgggttccgg cttgatgcc tcaagcatat taagttcagt     720 tttttttcctg attggttgtc gtatgtgcgt tctcagactg gcaagccgct atttaccgtc     780
ggggaatatt ggagctatga catcaacaag ttgcacaatt acattacgaa aacaaacgga     840
acgatgtctt tgtttgatgc cccgttacac aacaaatttt ataccgcttc caaatcaggg     900
ggcgcatttg atatgcgcac gttaatgacc aatactctca tgaaagatca accgacattg     960
gccgtcacct tcgttgataa tcatgacacc gaaccggcc aagcgctgca gtcatgggtc    1020
gacccatggt tcaaaccgtt ggcttacgcc tttattctaa ctcggcagga aggatacccg    1080
tgcgtctttt atggtgacta ttatggcatt ccacaatata acattccttc gctgaaaagc    1140
aaaatcgatc cgctcctcat cgcgcgcagg gattatgctt acgaacgca acatgattat    1200 cttgatcact ccgacatcat cggtggaca agggaagggg gcactgaaaa accaggatcc    1260
ggactggccg cactgatcac cgatgggccg ggaggaagca aatggatgta cgttggcaaa    1320
caacacgctg gaaaagtgtt ctatgacctt accggcaacc ggagtgacac cgtcaccatc    1380
aacagtgatg gatgggggga attcaaagtc aatggcggtt cggtttcggt ttgggttcct    1440
agaaaaacga ccgtttctac catcgctcgg ccgatcacaa cccgaccgtg gactggtgaa    1500
ttcgtccgtt ggaccgaacc acggttggtg gcatggcctt ga                       1542
```

```
<210> SEQ ID NO 2
<211> LENGTH: 513
<212> TYPE: PRT
<213> ORGANISM: Geobacillus stearothermophilus

<400> SEQUENCE: 2

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
    130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Lys Ala Trp Asp Trp Glu Val Asp Thr Glu Phe Gly
            180                 185                 190

Asn Tyr Asp Tyr Leu Met Tyr Ala Asp Leu Asp Met Asp His Pro Glu
        195                 200                 205

Val Val Thr Glu Leu Lys Asn Trp Gly Lys Trp Tyr Val Asn Thr Thr
    210                 215                 220

Asn Ile Asp Gly Phe Arg Leu Asp Ala Val Lys His Ile Lys Phe Ser
225                 230                 235                 240

Phe Phe Pro Asp Trp Leu Ser Tyr Val Arg Ser Gln Thr Gly Lys Pro
                245                 250                 255

Leu Phe Thr Val Gly Glu Tyr Trp Ser Tyr Asp Ile Asn Lys Leu His
            260                 265                 270

Asn Tyr Ile Thr Lys Thr Asn Gly Thr Met Ser Leu Phe Asp Ala Pro
        275                 280                 285

Leu His Asn Lys Phe Tyr Thr Ala Ser Lys Ser Gly Gly Ala Phe Asp
    290                 295                 300

Met Arg Thr Leu Met Thr Asn Thr Leu Met Lys Asp Gln Pro Thr Leu
305                 310                 315                 320

Ala Val Thr Phe Val Asp Asn His Asp Thr Glu Pro Gly Gln Ala Leu
                325                 330                 335

Gln Ser Trp Val Asp Pro Trp Phe Lys Pro Leu Ala Tyr Ala Phe Ile
            340                 345                 350

Leu Thr Arg Gln Glu Gly Tyr Pro Cys Val Phe Tyr Gly Asp Tyr Tyr
        355                 360                 365

Gly Ile Pro Gln Tyr Asn Ile Pro Ser Leu Lys Ser Lys Ile Asp Pro
    370                 375                 380
```

```
Leu Leu Ile Ala Arg Arg Asp Tyr Ala Tyr Gly Thr Gln His Asp Tyr
385                 390                 395                 400

Leu Asp His Ser Asp Ile Ile Gly Trp Thr Arg Glu Gly Gly Thr Glu
            405                 410                 415

Lys Pro Gly Ser Gly Leu Ala Ala Leu Ile Thr Asp Gly Pro Gly Gly
            420                 425                 430

Ser Lys Trp Met Tyr Val Gly Lys Gln His Ala Gly Lys Val Phe Tyr
            435                 440                 445

Asp Leu Thr Gly Asn Arg Ser Asp Thr Val Thr Ile Asn Ser Asp Gly
            450                 455                 460

Trp Gly Glu Phe Lys Val Asn Gly Gly Ser Val Ser Val Trp Val Pro
465                 470                 475                 480

Arg Lys Thr Thr Val Ser Thr Ile Ala Arg Pro Ile Thr Thr Arg Pro
                485                 490                 495

Trp Thr Gly Glu Phe Val Arg Trp Thr Glu Pro Arg Leu Val Ala Trp
            500                 505                 510

Pro

<210> SEQ ID NO 3
<211> LENGTH: 1455
<212> TYPE: DNA
<213> ORGANISM: Artificial Sequence
<220> FEATURE:
<223> OTHER INFORMATION: Alpha amylase variant

<400> SEQUENCE: 3
gtgaacggca ccatgatgca gtattttgaa tggtacttgc cggatgatgg cacgttatgg      60
accaaagtgg ccaatgaagc caacaactta tccagccttg catcaccgc  tctttggctg     120 ccgcccgctt acaaggaac  aagccgcagc gacgtagggt acggagtata cgacttgtat     180
gacctcggcg aattcaatca aaagggacc  gtccgcacaa atacggaac  aaaagctcaa     240 tatcttcaag ccattcaagc cgcccacgcc gctggaatgc aagtgtacgc cgatgtcgtg     300
ttcgaccata aggcggcgc  tgacggcacg gaatgggtgg acgccgtcga agtcaatccg     360
tccgaccgca accaagaaat ctcgggcacc tatcaaatcc aagcatggac gaaatttgat     420
tttcccgggc ggggcaacac ctactccagc tttaagtggc gctggtacca ttttgacggc     480
gttgattggg acgaaagccg aaaattgagc cgcatttaca aattccgcgg caaagcgtgg     540
gattgggaag tagacacgga atttggaaac tatgactact taatgtatgc cgaccttgat     600
atggatcatc ccgaagtcgt gaccgagctg aaaaactggg ggaaatggta tgtcaacaca     660
acgaacattg atgggttccg gcttgatgcc gtcaagcata ttaagttcag ttttttttcct     720 gattggttgt cgtatgtgcg ttctcagact ggcaagccgc tatttaccgt cggggaatat     780
tggagctatg acatcaacaa gttgcacaat tacattacga aaacaaacgg aacgatgtct     840
ttgtttgatg ccccgttaca caacaaattt tataccgctt ccaaatcagg ggcgcatttt     900
gatatgcgca cgttaatgac caatactctc atgaaagatc aaccgacatt ggccgtcacc     960
ttcgttgata tcatgacac  cgaacccggc caagcgctgc agtcatgggt cgacccatgg    1020
ttcaaaccgt ggcttacgc  ctttattcta actcggcagg aaggataccc gtgcgtcttt    1080
tatggtgact attatggcat ccacaatat  aacattcctt cgctgaaaag caaaatcgat    1140
ccgctcctca tcgcgcgcag ggattatgct tacggaacgc aacatgatta tcttgatcac    1200
tccgacatca tcgggtggac aagggaaggg ggcactgaaa aaccaggatc cggactggcc    1260
gcactgatca ccgatgggcc gggaggaagc aaatggatgt acgttggcaa acaacacgct    1320
```

```
ggaaaagtgt tctatgacct taccggcaac cggagtgaca ccgtcaccat caacagtgat    1380 ggatggggg aattcaaagt caatggcggt tcggtttcgg tttgggttcc tagaaaaacg     1440
accgtttctt aataa                                                     1455
```

<210> SEQ ID NO 4
<211> LENGTH: 483
<212> TYPE: PRT
<213> ORGANISM: Artificial Sequence
<220> FEATURE:
<223> OTHER INFORMATION: Alpha amylase variant

<400> SEQUENCE: 4

```
Val Asn Gly Thr Met Met Gln Tyr Phe Glu Trp Tyr Leu Pro Asp Asp
1               5                   10                  15

Gly Thr Leu Trp Thr Lys Val Ala Asn Glu Ala Asn Asn Leu Ser Ser
            20                  25                  30

Leu Gly Ile Thr Ala Leu Trp Leu Pro Pro Ala Tyr Lys Gly Thr Ser
        35                  40                  45

Arg Ser Asp Val Gly Tyr Gly Val Tyr Asp Leu Tyr Asp Leu Gly Glu
    50                  55                  60

Phe Asn Gln Lys Gly Thr Val Arg Thr Lys Tyr Gly Thr Lys Ala Gln
65                  70                  75                  80

Tyr Leu Gln Ala Ile Gln Ala Ala His Ala Ala Gly Met Gln Val Tyr
                85                  90                  95

Ala Asp Val Val Phe Asp His Lys Gly Gly Ala Asp Gly Thr Glu Trp
            100                 105                 110

Val Asp Ala Val Glu Val Asn Pro Ser Asp Arg Asn Gln Glu Ile Ser
        115                 120                 125

Gly Thr Tyr Gln Ile Gln Ala Trp Thr Lys Phe Asp Phe Pro Gly Arg
    130                 135                 140

Gly Asn Thr Tyr Ser Ser Phe Lys Trp Arg Trp Tyr His Phe Asp Gly
145                 150                 155                 160

Val Asp Trp Asp Glu Ser Arg Lys Leu Ser Arg Ile Tyr Lys Phe Arg
                165                 170                 175

Gly Lys Ala Trp Asp Trp Glu Val Asp Thr Glu Phe Gly Asn Tyr Asp
            180                 185                 190

Tyr Leu Met Tyr Ala Asp Leu Asp Met Asp His Pro Glu Val Val Thr
        195                 200                 205

Glu Leu Lys Asn Trp Gly Lys Trp Tyr Val Asn Thr Thr Asn Ile Asp
    210                 215                 220

Gly Phe Arg Leu Asp Ala Val Lys His Ile Lys Phe Ser Phe Phe Pro
225                 230                 235                 240

Asp Trp Leu Ser Tyr Val Arg Ser Gln Thr Gly Lys Pro Leu Phe Thr
                245                 250                 255

Val Gly Glu Tyr Trp Ser Tyr Asp Ile Asn Lys Leu His Asn Tyr Ile
            260                 265                 270

Thr Lys Thr Asn Gly Thr Met Ser Leu Phe Asp Ala Pro Leu His Asn
        275                 280                 285

Lys Phe Tyr Thr Ala Ser Lys Ser Gly Gly Ala Phe Asp Met Arg Thr
    290                 295                 300

Leu Met Thr Asn Thr Leu Met Lys Asp Gln Pro Thr Leu Ala Val Thr
305                 310                 315                 320

Phe Val Asp Asn His Asp Thr Glu Pro Gly Gln Ala Leu Gln Ser Trp
                325                 330                 335
```

```
Val Asp Pro Trp Phe Lys Pro Leu Ala Tyr Ala Phe Ile Leu Thr Arg
            340                 345                 350

Gln Glu Gly Tyr Pro Cys Val Phe Tyr Gly Asp Tyr Tyr Gly Ile Pro
        355                 360                 365

Gln Tyr Asn Ile Pro Ser Leu Lys Ser Lys Ile Asp Pro Leu Leu Ile
    370                 375                 380

Ala Arg Arg Asp Tyr Ala Tyr Gly Thr Gln His Asp Tyr Leu Asp His
385                 390                 395                 400

Ser Asp Ile Ile Gly Trp Thr Arg Glu Gly Thr Glu Lys Pro Gly
                405                 410                 415

Ser Gly Leu Ala Ala Leu Ile Thr Asp Gly Pro Gly Gly Ser Lys Trp
            420                 425                 430

Met Tyr Val Gly Lys Gln His Ala Gly Lys Val Phe Tyr Asp Leu Thr
        435                 440                 445

Gly Asn Arg Ser Asp Thr Val Thr Ile Asn Ser Asp Gly Trp Gly Glu
    450                 455                 460

Phe Lys Val Asn Gly Gly Ser Val Ser Val Trp Val Pro Arg Lys Thr
465                 470                 475                 480

Thr Val Ser

<210> SEQ ID NO 5
<211> LENGTH: 1461
<212> TYPE: DNA
<213> ORGANISM: Artificial Sequence
<220> FEATURE:
<223> OTHER INFORMATION: Alpha amylase variant

<400> SEQUENCE: 5
gccaatctta acggcaccat gatgcagtat tttgaatggt acttgccgga tgatggcacg        60
ttatggacca agtggccaa tgaagccaac aacttatcca gccttggcat caccgctctt       120
tggctgccgc cgcttacaa aggaacaagc cgcagcgacg tagggtacgg agtatacgac       180
ttgtatgacc tcggcgaatt caatcaaaaa gggaccgtcc gcacaaaata cggaacaaaa       240
gctcaatatc ttcaagccat tcaagccgcc cacgccgctg aatgcaagt gtacgccgat       300 gtcgtgttcg accataaagg cggcgctgac ggcacggaat gggtgacgc cgtcgaagtc       360 aatccgtccg accgcaacca gaaatctcg ggcacctatc aaatccaagc atggacgaaa       420 tttgatttc ccgggcgggg caacacctac tccagcttta gtggcgctg gtaccatttt       480 gacggcgttg attgggacga agccgaaaa ttgagccgca tttacaaatt ccgcggcaaa       540
gcgtgggatt gggaagtaga cacggaattt ggaaactatg actacttaat gtatgccgac       600
cttgatatgg atcatcccga agtcgtgacc gagctgaaaa actgggggaa atggtatgtc       660
aacacaacga acattgatgg gttccggctt gatgccgtca gcatattaa gttcagtttt       720 tttcctgatt ggttgtcgta tgtgcgttct cagactggca agccgctatt taccgtcggg       780
gaatattgga gctatgacat caacaagttg cacaattaca ttacgaaaac aaacggaacg       840 atgtcttgt tgatgcccc gttacacaac aaattttata ccgcttccaa atcagggggc       900
gcatttgata tgcgcacgtt aatgaccaat actctcatga agatcaacc gacattggcc       960 gtcaccttcg ttgataatca tgacaccgaa cccggccaag cgctgcagtc atgggtcgac      1020
ccatggttca aaccgttggc ttacgccttt attctaactc ggcaggaagg ataccccgtgc      1080 gtcttttatg gtgactatta tggcattcca caatataaca ttccttcgct gaaaagcaaa      1140
atcgatccgc tcctcatcgc gcgcagggat tatgcttacg gaacgcaaca tgattatctt      1200
```

```
gatcactccg acatcatcgg gtggacaagg aaggggggca ctgaaaaacc aggatccgga    1260
ctggccgcac tgatcaccga tgggccggga ggaagcaaat ggatgtacgt tggcaaacaa    1320
cacgctggaa aagtgttcta tgaccttacc ggcaaccgga gtgacaccgt caccatcaac    1380
agtgatggat gggggggaatt caaagtcaat ggcggttcgg tttcggtttg ggttcctaga    1440
aaaacgaccg tttcttaata a                                              1461
```

```
<210> SEQ ID NO 6
<211> LENGTH: 485
<212> TYPE: PRT
<213> ORGANISM: Artificial Sequence
<220> FEATURE:
<223> OTHER INFORMATION: Alpha amylase variant

<400> SEQUENCE: 6

Ala Asn Leu Asn Gly Thr Met Met Gln Tyr Phe Glu Trp Tyr Leu Pro
1               5                   10                  15

Asp Asp Gly Thr Leu Trp Thr Lys Val Ala Asn Glu Ala Asn Asn Leu
            20                  25                  30

Ser Ser Leu Gly Ile Thr Ala Leu Trp Leu Pro Pro Ala Tyr Lys Gly
        35                  40                  45

Thr Ser Arg Ser Asp Val Gly Tyr Gly Val Tyr Asp Leu Tyr Asp Leu
    50                  55                  60

Gly Glu Phe Asn Gln Lys Gly Thr Val Arg Thr Lys Tyr Gly Thr Lys
65                  70                  75                  80

Ala Gln Tyr Leu Gln Ala Ile Gln Ala Ala His Ala Ala Gly Met Gln
                85                  90                  95

Val Tyr Ala Asp Val Val Phe Asp His Lys Gly Gly Ala Asp Gly Thr
            100                 105                 110

Glu Trp Val Asp Ala Val Glu Val Asn Pro Ser Asp Arg Asn Gln Glu
        115                 120                 125

Ile Ser Gly Thr Tyr Gln Ile Gln Ala Trp Thr Lys Phe Asp Phe Pro
    130                 135                 140

Gly Arg Gly Asn Thr Tyr Ser Ser Phe Lys Trp Arg Trp Tyr His Phe
145                 150                 155                 160

Asp Gly Val Asp Trp Asp Glu Ser Arg Lys Leu Ser Arg Ile Tyr Lys
                165                 170                 175

Phe Arg Gly Lys Ala Trp Asp Trp Glu Val Asp Thr Glu Phe Gly Asn
            180                 185                 190

Tyr Asp Tyr Leu Met Tyr Ala Asp Leu Asp Met Asp His Pro Glu Val
        195                 200                 205

Val Thr Glu Leu Lys Asn Trp Gly Lys Trp Tyr Val Asn Thr Thr Asn
    210                 215                 220

Ile Asp Gly Phe Arg Leu Asp Ala Val Lys His Ile Lys Phe Ser Phe
225                 230                 235                 240

Phe Pro Asp Trp Leu Ser Tyr Val Arg Ser Gln Thr Gly Lys Pro Leu
                245                 250                 255

Phe Thr Val Gly Glu Tyr Trp Ser Tyr Asp Ile Asn Lys Leu His Asn
            260                 265                 270

Tyr Ile Thr Lys Thr Asn Gly Thr Met Ser Leu Phe Asp Ala Pro Leu
        275                 280                 285

His Asn Lys Phe Tyr Thr Ala Ser Lys Ser Gly Gly Ala Phe Asp Met
    290                 295                 300

Arg Thr Leu Met Thr Asn Thr Leu Met Lys Asp Gln Pro Thr Leu Ala
305                 310                 315                 320
```

```
Val Thr Phe Val Asp Asn His Asp Thr Glu Pro Gly Gln Ala Leu Gln
            325                 330                 335

Ser Trp Val Asp Pro Trp Phe Lys Pro Leu Ala Tyr Ala Phe Ile Leu
            340                 345                 350

Thr Arg Gln Glu Gly Tyr Pro Cys Val Phe Tyr Gly Asp Tyr Tyr Gly
            355                 360                 365

Ile Pro Gln Tyr Asn Ile Pro Ser Leu Lys Ser Lys Ile Asp Pro Leu
            370                 375                 380

Leu Ile Ala Arg Arg Asp Tyr Ala Tyr Gly Thr Gln His Asp Tyr Leu
385                 390                 395                 400

Asp His Ser Asp Ile Ile Gly Trp Thr Arg Glu Gly Gly Thr Glu Lys
                405                 410                 415

Pro Gly Ser Gly Leu Ala Ala Leu Ile Thr Asp Gly Pro Gly Gly Ser
                420                 425                 430

Lys Trp Met Tyr Val Gly Lys Gln His Ala Gly Lys Val Phe Tyr Asp
                435                 440                 445

Leu Thr Gly Asn Arg Ser Asp Thr Val Thr Ile Asn Ser Asp Gly Trp
            450                 455                 460

Gly Glu Phe Lys Val Asn Gly Gly Ser Val Ser Val Trp Val Pro Arg
465                 470                 475                 480

Lys Thr Thr Val Ser
                485

<210> SEQ ID NO 7
<211> LENGTH: 1455
<212> TYPE: DNA
<213> ORGANISM: Artificial Sequence
<220> FEATURE:
<223> OTHER INFORMATION: Alpha amylase variant

<400> SEQUENCE: 7
gccaatctta acggcaccat gatgcagtat tttgaatggt acttgccgga tgatggcacg     60
ttatggacca aagtggccaa tgaagccaac aacttatcca gccttggcat caccgctctt    120
tggctgccgc ccgcttacaa aggaacaagc cgcagcgacg tagggtacgg agtatacgac    180
ttgtatgacc tcggcgaatt caatcaaaaa gggaccgtcc gcacaaaata cggaacaaaa    240
gctcaatatc ttcaagccat tcaagccgcc cacgccgctg gaatgcaagt gtacgccgat    300
gtcgtgttcg accataaagg cggcgctgac ggcacggaat gggtgacgc cgtcgaagtc    360 aatccgtccg accgcaacca agaaatctcg ggcacctatc aaatccaagc atggacgaaa    420
tttgattttc cgggcgggg caacacctac tccagcttta gtggcgctg gtaccatttt    480 gacggcgttg attgggacga aagccgaaaa ttgagccgca tttacaaatt ccgcggcaaa    540
gcgtgggatt gggaagtaga cacggaattt ggaaactatg actacttaat gtatgccgac    600
cttgatatgg atcatcccga agtcgtgacc gagctgaaaa actggggggaa atggtatgtc    660 aacacaacga acattgatgg gttccggctt gatgccgtca gcatattaa gttcagtttt    720 tttcctgatt ggttgtcgta tgtgcgttct cagactggca agccgctatt taccgtcggg    780
gaatattgga gctatgacat caacaagttg cacaattaca ttcgaaaaac aaacggaacg    840
atgtctttgt ttgatgcccc gttacacaac aaatttttata ccgcttccaa atcagggggc    900
gcatttgata tgcgcacgtt aatgaccaat actctcatga agatcaacc gacattggcc    960 gtcaccttcg ttgataatca tgacaccgaa cccggccaag cgctgcagtc atgggtcgac   1020
ccatggttca aaccgttggc ttacgccttt attctaactc ggcaggaagg atacccgtgc   1080
```

-continued

```
gtcttttatg gtgactatta tggcattcca caatataaca ttccttcgct gaaaagcaaa    1140
atcgatccgc tcctcatcgc gcgcagggat tatgcttacg gaacgcaaca tgattatctt    1200
gatcactccg acatcatcgg gtggacaagg aagggggca ctgaaaaacc aggatccgga     1260
ctggccgcac tgatcaccga tgggccggga ggaagcaaat ggatgtacgt tgcaaacaa     1320 cacgctggaa aagtgttcta tgaccttacc ggcaaccgga gtgacaccgt caccatcaac    1380
agtgatggat gggggaatt caaagtcaat ggcggttcgg tttcggtttg ggttcctaga     1440
aaaacgacct aataa                                                     1455
```

<210> SEQ ID NO 8
<211> LENGTH: 483
<212> TYPE: PRT
<213> ORGANISM: Artificial Sequence
<220> FEATURE:
<223> OTHER INFORMATION: Alpha amylase variant

<400> SEQUENCE: 8

```
Ala Asn Leu Asn Gly Thr Met Met Gln Tyr Phe Glu Trp Tyr Leu Pro
1               5                   10                  15

Asp Asp Gly Thr Leu Trp Thr Lys Val Ala Asn Glu Ala Asn Asn Leu
            20                  25                  30

Ser Ser Leu Gly Ile Thr Ala Leu Trp Leu Pro Pro Ala Tyr Lys Gly
        35                  40                  45

Thr Ser Arg Ser Asp Val Gly Tyr Gly Val Tyr Asp Leu Tyr Asp Leu
    50                  55                  60

Gly Glu Phe Asn Gln Lys Gly Thr Val Arg Thr Lys Tyr Gly Thr Lys
65                  70                  75                  80

Ala Gln Tyr Leu Gln Ala Ile Gln Ala Ala His Ala Ala Gly Met Gln
                85                  90                  95

Val Tyr Ala Asp Val Val Phe Asp His Lys Gly Gly Ala Asp Gly Thr
            100                 105                 110

Glu Trp Val Asp Ala Val Glu Val Asn Pro Ser Asp Arg Asn Gln Glu
        115                 120                 125

Ile Ser Gly Thr Tyr Gln Ile Gln Ala Trp Thr Lys Phe Asp Phe Pro
    130                 135                 140

Gly Arg Gly Asn Thr Tyr Ser Ser Phe Lys Trp Arg Trp Tyr His Phe
145                 150                 155                 160

Asp Gly Val Asp Trp Asp Glu Ser Arg Lys Leu Ser Arg Ile Tyr Lys
                165                 170                 175

Phe Arg Gly Lys Ala Trp Asp Trp Glu Val Asp Thr Glu Phe Gly Asn
            180                 185                 190

Tyr Asp Tyr Leu Met Tyr Ala Asp Leu Asp Met Asp His Pro Glu Val
        195                 200                 205

Val Thr Glu Leu Lys Asn Trp Gly Lys Trp Tyr Val Asn Thr Thr Asn
    210                 215                 220

Ile Asp Gly Phe Arg Leu Asp Ala Val Lys His Ile Lys Phe Ser Phe
225                 230                 235                 240

Phe Pro Asp Trp Leu Ser Tyr Val Arg Ser Gln Thr Gly Lys Pro Leu
                245                 250                 255

Phe Thr Val Gly Glu Tyr Trp Ser Tyr Asp Ile Asn Lys Leu His Asn
            260                 265                 270

Tyr Ile Thr Lys Thr Asn Gly Thr Met Ser Leu Phe Asp Ala Pro Leu
        275                 280                 285
```

-continued

```
His Asn Lys Phe Tyr Thr Ala Ser Lys Ser Gly Gly Ala Phe Asp Met
    290                 295                 300

Arg Thr Leu Met Thr Asn Thr Leu Met Lys Asp Gln Pro Thr Leu Ala
305                 310                 315                 320

Val Thr Phe Val Asp Asn His Asp Thr Glu Pro Gly Gln Ala Leu Gln
                325                 330                 335

Ser Trp Val Asp Pro Trp Phe Lys Pro Leu Ala Tyr Ala Phe Ile Leu
                340                 345                 350

Thr Arg Gln Glu Gly Tyr Pro Cys Val Phe Tyr Gly Asp Tyr Tyr Gly
                355                 360                 365

Ile Pro Gln Tyr Asn Ile Pro Ser Leu Lys Ser Lys Ile Asp Pro Leu
370                 375                 380

Leu Ile Ala Arg Arg Asp Tyr Ala Tyr Gly Thr Gln His Asp Tyr Leu
385                 390                 395                 400

Asp His Ser Asp Ile Ile Gly Trp Thr Arg Glu Gly Thr Glu Lys
                405                 410                 415

Pro Gly Ser Gly Leu Ala Ala Leu Ile Thr Asp Gly Pro Gly Gly Ser
                420                 425                 430

Lys Trp Met Tyr Val Gly Lys Gln His Ala Gly Lys Val Phe Tyr Asp
                435                 440                 445

Leu Thr Gly Asn Arg Ser Asp Thr Val Thr Ile Asn Ser Asp Gly Trp
450                 455                 460

Gly Glu Phe Lys Val Asn Gly Gly Ser Val Ser Val Trp Val Pro Arg
465                 470                 475                 480

Lys Thr Thr
```

<210> SEQ ID NO 9
<211> LENGTH: 1446
<212> TYPE: DNA
<213> ORGANISM: Artificial Sequence
<220> FEATURE:
<223> OTHER INFORMATION: Alpha amylase variant

<400> SEQUENCE: 9

```
gccaatctta acggcaccat gatgcagtat tttgaatggt acttgccgga tgatggcacg      60
ttatggacca agtggccaa tgaagccaac aacttatcca gccttggcat caccgctctt     120
tggctgccgc cgcttacaa aggaacaagc cgcagcgacg tagggtacgg agtatacgac     180
ttgtatgacc tcggcgaatt caatcaaaaa gggaccgtcc gcacaaaata cggaacaaaa     240
gctcaatatc ttcaagccat tcaagccgcc cacgccgctg aatgcaagt gtacgccgat     300
gtcgtgttcg accataaagg cggcgctgac ggcacggaat gggtggacgc cgtcgaagtc     360
aatccgtccg accgcaacca agaaatctcg ggcacctatc aaatccaagc atggacgaaa     420
tttgattttc ccgggcgggg caacacctac tccagcttta gtggcgctg gtaccatttt     480
gacggcgttg attgggacga agccgaaaa ttgagccgca tttacaaatt ccgcggcaaa     540
gcgtgggatt gggaagtaga cacggaattt ggaaactatg actacttaat gtatgccgac     600
cttgatatgg atcatcccga agtcgtgacc gagctgaaaa actgggggaa atggtatgtc     660
aacacaacga acattgatgg gttccggctt gatgccgtca gcatattaa gttcagtttt     720
tttcctgatt ggttgtcgta tgtgcgttct cagactggca agccgctatt taccgtcggg     780
gaatattgga gctatgacat caacaagttg cacaattaca ttacgaaaac aaacggaacg     840
atgtctttgt tgatgccccc gttacacaac aaatttttata ccgcttccaa atcaggggc     900
gcatttgata tgcgcacgtt aatgaccaat actctcatga aagatcaacc gacattggcc     960
```

-continued

```
gtcaccttcg ttgataatca tgacaccgaa cccggccaag cgctgcagtc atgggtcgac    1020
ccatggttca aaccgttggc ttacgccttt attctaactc ggcaggaagg atacccgtgc    1080
gtcttttatg gtgactatta tggcattcca caatataaca ttccttcgct gaaaagcaaa    1140
atcgatccgc tcctcatcgc gcgcagggat tatgcttacg aacgcaaca tgattatctt    1200 gatcactccg acatcatcgg gtggacaagg aagggggca ctgaaaaacc aggatccgga    1260
ctggccgcac tgatcaccga tgggccggga ggaagcaaat ggatgtacgt tggcaaacaa    1320
cacgctggaa aagtgttcta tgaccttacc ggcaaccgga gtgacaccgt caccatcaac    1380
agtgatggat gggggaatt caaagtcaat ggcggttcgg tttcggtttg ggttcctaga    1440
taataa                                                                1446
```

<210> SEQ ID NO 10
<211> LENGTH: 480
<212> TYPE: PRT
<213> ORGANISM: Artificial Sequence
<220> FEATURE:
<223> OTHER INFORMATION: Alpha amylase variant

<400> SEQUENCE: 10

```
Ala Asn Leu Asn Gly Thr Met Met Gln Tyr Phe Glu Trp Tyr Leu Pro
1               5                   10                  15

Asp Asp Gly Thr Leu Trp Thr Lys Val Ala Asn Glu Ala Asn Asn Leu
            20                  25                  30

Ser Ser Leu Gly Ile Thr Ala Leu Trp Leu Pro Pro Ala Tyr Lys Gly
        35                  40                  45

Thr Ser Arg Ser Asp Val Gly Tyr Gly Val Tyr Asp Leu Tyr Asp Leu
    50                  55                  60

Gly Glu Phe Asn Gln Lys Gly Thr Val Arg Thr Lys Tyr Gly Thr Lys
65                  70                  75                  80

Ala Gln Tyr Leu Gln Ala Ile Gln Ala Ala His Ala Ala Gly Met Gln
                85                  90                  95

Val Tyr Ala Asp Val Val Phe Asp His Lys Gly Gly Ala Asp Gly Thr
            100                 105                 110

Glu Trp Val Asp Ala Val Glu Val Asn Pro Ser Asp Arg Asn Gln Glu
        115                 120                 125

Ile Ser Gly Thr Tyr Gln Ile Gln Ala Trp Thr Lys Phe Asp Phe Pro
    130                 135                 140

Gly Arg Gly Asn Thr Tyr Ser Ser Phe Lys Trp Arg Trp Tyr His Phe
145                 150                 155                 160

Asp Gly Val Asp Trp Asp Glu Ser Arg Lys Leu Ser Arg Ile Tyr Lys
                165                 170                 175

Phe Arg Gly Lys Ala Trp Asp Trp Glu Val Asp Thr Glu Phe Gly Asn
            180                 185                 190

Tyr Asp Tyr Leu Met Tyr Ala Asp Leu Asp Met Asp His Pro Glu Val
        195                 200                 205

Val Thr Glu Leu Lys Asn Trp Gly Lys Trp Tyr Val Asn Thr Thr Asn
    210                 215                 220

Ile Asp Gly Phe Arg Leu Asp Ala Val Lys His Ile Lys Phe Ser Phe
225                 230                 235                 240

Phe Pro Asp Trp Leu Ser Tyr Val Arg Ser Gln Thr Gly Lys Pro Leu
                245                 250                 255

Phe Thr Val Gly Glu Tyr Trp Ser Tyr Asp Ile Asn Lys Leu His Asn
            260                 265                 270
```

```
Tyr Ile Thr Lys Thr Asn Gly Thr Met Ser Leu Phe Asp Ala Pro Leu
            275                 280                 285

His Asn Lys Phe Tyr Thr Ala Ser Lys Ser Gly Gly Ala Phe Asp Met
        290                 295                 300

Arg Thr Leu Met Thr Asn Thr Leu Met Lys Asp Gln Pro Thr Leu Ala
305                 310                 315                 320

Val Thr Phe Val Asp Asn His Asp Thr Glu Pro Gly Gln Ala Leu Gln
                325                 330                 335

Ser Trp Val Asp Pro Trp Phe Lys Pro Leu Ala Tyr Ala Phe Ile Leu
            340                 345                 350

Thr Arg Gln Glu Gly Tyr Pro Cys Val Phe Tyr Gly Asp Tyr Tyr Gly
        355                 360                 365

Ile Pro Gln Tyr Asn Ile Pro Ser Leu Lys Ser Lys Ile Asp Pro Leu
    370                 375                 380

Leu Ile Ala Arg Arg Asp Tyr Ala Tyr Gly Thr Gln His Asp Tyr Leu
385                 390                 395                 400

Asp His Ser Asp Ile Ile Gly Trp Thr Arg Glu Gly Gly Thr Glu Lys
                405                 410                 415

Pro Gly Ser Gly Leu Ala Ala Leu Ile Thr Asp Gly Pro Gly Gly Ser
            420                 425                 430

Lys Trp Met Tyr Val Gly Lys Gln His Ala Gly Lys Val Phe Tyr Asp
        435                 440                 445

Leu Thr Gly Asn Arg Ser Asp Thr Val Thr Ile Asn Ser Asp Gly Trp
    450                 455                 460

Gly Glu Phe Lys Val Asn Gly Gly Ser Val Ser Val Trp Val Pro Arg
465                 470                 475                 480

<210> SEQ ID NO 11
<211> LENGTH: 1470
<212> TYPE: DNA
<213> ORGANISM: Artificial Sequence
<220> FEATURE:
<223> OTHER INFORMATION: Artificial sequence

<400> SEQUENCE: 11
gccaatctta acggcaccat gatgcagtat tttgaatggt acttgccgga tgatggcacg      60
ttatggacca aagtggccaa tgaagccaac aacttatcca gccttggcat caccgctctt     120
tggctgccgc ccgcttacaa aggaacaagc cgcagcgacg tagggtacgg agtatacgac     180
ttgtatgacc tcggcgaatt caatcaaaaa gggaccgtcc gcacaaaata cggaacaaaa     240
gctcaatatc ttcaagccat tcaagccgcc cacgccgctg gaatgcaagt gtacgccgat     300
gtcgtgttcg accataaagg cggcgctgac ggcacggaat gggtgacgc cgtcgaagtc      360 aatccgtccg accgcaacca agaaatctcg ggcacctatc aaatccaagc atggacgaaa     420
tttgattttc ccgggcgggg caacacctac tccagcttta gtggcgctg gtaccatttt      480 gacggcgttg attgggacga aagccgaaaa ttgagccgca tttacaaatt ccgcggcaaa     540
gcgtgggatt gggaagtaga cacggaattt ggaaactatg actacttaat gtatgccgac     600
cttgatatgg atcatcccga agtcgtgacc gagctgaaaa actgggggaa atggtatgtc     660
aacacaacga acattgatgg gttccggctt gatgccgtca agcatattaa gttcagtttt     720
tttcctgatt ggttgtcgta tgtgcgttct cagactggca agccgctatt taccgtcggg     780
gaatattgga gctatgacat caacaagttg cacaattaca ttacgaaaac aaacggaacg     840
atgtctttgt tgatgccccc gttacacaac aaatttttata ccgcttccaa atcagggggc     900
```

-continued

```
gcatttgata tgcgcacgtt aatgaccaat actctcatga aagatcaacc gacattggcc    960
gtcaccttcg ttgataatca tgacaccgaa cccggccaag cgctgcagtc atgggtcgac   1020
ccatggttca aaccgttggc ttacgccttt attctaactc ggcaggaagg atacccgtgc   1080
gtcttttatg gtgactatta tggcattcca caatataaca ttccttcgct gaaaagcaaa   1140
atcgatccgc tcctcatcgc gcgcagggat tatgcttacg aacgcaaca tgattatctt    1200
gatcactccg acatcatcgg gtggacaagg gaaggggggca ctgaaaaacc aggatccgga   1260
ctggccgcac tgatcaccga tgggccggga ggaagcaaat ggatgtacgt tggcaaacaa   1320
cacgctggaa aagtgttcta tgaccttacc ggcaaccgga gtgacaccgt caccatcaac   1380
agtgatggat gggggggaatt caaagtcaat ggcggttcgg tttcggtttg ggttcctaga   1440
aaaacgaccg tttctttgc taactaataa                                    1470
```

<210> SEQ ID NO 12
<211> LENGTH: 488
<212> TYPE: PRT
<213> ORGANISM: Artificial Sequence
<220> FEATURE:
<223> OTHER INFORMATION: Artificial sequence

<400> SEQUENCE: 12

```
Ala Asn Leu Asn Gly Thr Met Met Gln Tyr Phe Glu Trp Tyr Leu Pro
1               5                   10                  15

Asp Asp Gly Thr Leu Trp Thr Lys Val Ala Asn Glu Ala Asn Asn Leu
            20                  25                  30

Ser Ser Leu Gly Ile Thr Ala Leu Trp Leu Pro Pro Ala Tyr Lys Gly
        35                  40                  45

Thr Ser Arg Ser Asp Val Gly Tyr Gly Val Tyr Asp Leu Tyr Asp Leu
    50                  55                  60

Gly Glu Phe Asn Gln Lys Gly Thr Val Arg Thr Lys Tyr Gly Thr Lys
65                  70                  75                  80

Ala Gln Tyr Leu Gln Ala Ile Gln Ala Ala His Ala Ala Gly Met Gln
                85                  90                  95

Val Tyr Ala Asp Val Val Phe Asp His Lys Gly Gly Ala Asp Gly Thr
            100                 105                 110

Glu Trp Val Asp Ala Val Glu Val Asn Pro Ser Asp Arg Asn Gln Glu
        115                 120                 125

Ile Ser Gly Thr Tyr Gln Ile Gln Ala Trp Thr Lys Phe Asp Phe Pro
    130                 135                 140

Gly Arg Gly Asn Thr Tyr Ser Ser Phe Lys Trp Arg Trp Tyr His Phe
145                 150                 155                 160

Asp Gly Val Asp Trp Asp Glu Ser Arg Lys Leu Ser Arg Ile Tyr Lys
                165                 170                 175

Phe Arg Gly Lys Ala Trp Asp Trp Glu Val Asp Thr Glu Phe Gly Asn
            180                 185                 190

Tyr Asp Tyr Leu Met Tyr Ala Asp Leu Asp Met Asp His Pro Glu Val
        195                 200                 205

Val Thr Glu Leu Lys Asn Trp Gly Lys Trp Tyr Val Asn Thr Thr Asn
    210                 215                 220

Ile Asp Gly Phe Arg Leu Asp Ala Val Lys His Ile Lys Phe Ser Phe
225                 230                 235                 240

Phe Pro Asp Trp Leu Ser Tyr Val Arg Ser Gln Thr Gly Lys Pro Leu
                245                 250                 255
```

```
Phe Thr Val Gly Glu Tyr Trp Ser Tyr Asp Ile Asn Lys Leu His Asn
            260                 265                 270

Tyr Ile Thr Lys Thr Asn Gly Thr Met Ser Leu Phe Asp Ala Pro Leu
        275                 280                 285

His Asn Lys Phe Tyr Thr Ala Ser Lys Ser Gly Gly Ala Phe Asp Met
    290                 295                 300

Arg Thr Leu Met Thr Asn Thr Leu Met Lys Asp Gln Pro Thr Leu Ala
305                 310                 315                 320

Val Thr Phe Val Asp Asn His Asp Thr Glu Pro Gly Gln Ala Leu Gln
                325                 330                 335

Ser Trp Val Asp Pro Trp Phe Lys Pro Leu Ala Tyr Ala Phe Ile Leu
            340                 345                 350

Thr Arg Gln Glu Gly Tyr Pro Cys Val Phe Tyr Gly Asp Tyr Tyr Gly
        355                 360                 365

Ile Pro Gln Tyr Asn Ile Pro Ser Leu Lys Ser Lys Ile Asp Pro Leu
    370                 375                 380

Leu Ile Ala Arg Arg Asp Tyr Ala Tyr Gly Thr Gln His Asp Tyr Leu
385                 390                 395                 400

Asp His Ser Asp Ile Ile Gly Trp Thr Arg Glu Gly Thr Glu Lys
                405                 410                 415

Pro Gly Ser Gly Leu Ala Ala Leu Ile Thr Asp Gly Pro Gly Gly Ser
            420                 425                 430

Lys Trp Met Tyr Val Gly Lys Gln His Ala Gly Lys Val Phe Tyr Asp
        435                 440                 445

Leu Thr Gly Asn Arg Ser Asp Thr Val Thr Ile Asn Ser Asp Gly Trp
    450                 455                 460

Gly Glu Phe Lys Val Asn Gly Gly Ser Val Ser Val Trp Val Pro Arg
465                 470                 475                 480

Lys Thr Thr Val Ser Phe Ala Asn
                485

<210> SEQ ID NO 13
<211> LENGTH: 873
<212> TYPE: DNA
<213> ORGANISM: Artificial Sequence
<220> FEATURE:
<223> OTHER INFORMATION: Promoter sequence

<400> SEQUENCE: 13
ggtaccagct attgtaacat aatcggtacg ggggtgaaaa agctaacgga aaagggagcg    60 gaaagaatg atgtaagcgt gaaaattttt ttatcttatc acttgaaatt ggaagggaga    120
ttctttatta taagaaaacg gatgctgaag aaggaaacg aagtcggcaa ccattccctgg   180 gaccatccgt tattgacaag gctgtcaaat gaaaaagcgt atcaggagat taacgacacg    240
caagaaatga tcgaaaaaat cagcggacac ctgcctgtac acttgcgtcc tccatacggc    300
gggatcaatg attccgtccg ctcgctttcc aatctgaagg tttcattgtg ggatgttgat    360
ccggaagatt ggaagtacaa aaataagcaa aagattgtca atcatgtcat gagccatgcg    420
ggagacggaa aaatcgtctt aatgcacgat atttatgcaa cgtccgcaga tgctgctgaa    480
gagattatta aaaagctgaa agcaaaaggc tatcaattgg taactgtatc tcagcttgaa    540
gaagtgaaga agcagagagg ctattgaata aatgagtaga aagcgccata tcggcgcttt    600
tcttttggaa gaaatatag ggaaaatggt atttgttaaa aattctgaat atttatacaa    660
tatcatatgt ttcacaggga ggagaatcgg ccttaagggc ctgcaatcga ttgtttgaga    720
```

```
aaagaagaag accataaaaa taccttgtct gtcatcagac agggtatttt ttatgctgtc    780
cagactgtcc gctgtgtaaa aaaaaggaat aaaggggggt tgacattatt ttactgatat    840
gtataatata atttgtataa gaaaatggag ctc                                 873
```

<210> SEQ ID NO 14
<211> LENGTH: 98
<212> TYPE: DNA
<213> ORGANISM: Artificial Sequence
<220> FEATURE:
<223> OTHER INFORMATION: Synthetic termination sequence

<400> SEQUENCE: 14

```
tcaataataa taacgctgtg tgctttaagc acacagcgtt ttttagtgtg tatgaatcga    60
gatcctgagc gccggtcgct accattacca gttggtct                            98
```

<210> SEQ ID NO 15
<211> LENGTH: 96
<212> TYPE: DNA
<213> ORGANISM: Artificial Sequence
<220> FEATURE:
<223> OTHER INFORMATION: Native signal sequence

<400> SEQUENCE: 15

```
atgattcaaa aacgaaagcg gacagtttcg ttcagacttg tgcttatgtg cacgctgtta    60
tttgtcagtt tgccgattac aaaaacatca gccgca                              96
```

<210> SEQ ID NO 16
<211> LENGTH: 35
<212> TYPE: DNA
<213> ORGANISM: Artificial Sequence
<220> FEATURE:
<223> OTHER INFORMATION: lichApr_F1

<400> SEQUENCE: 16

```
ttattgagcg gcagcttcga cattgatcag acctt                               35
```

<210> SEQ ID NO 17
<211> LENGTH: 34
<212> TYPE: DNA
<213> ORGANISM: Artificial Sequence
<220> FEATURE:
<223> OTHER INFORMATION: lichApr_R1

<400> SEQUENCE: 17

```
ccttacggca ttcctctcaa cagcggatct tcag                                34
```

<210> SEQ ID NO 18
<211> LENGTH: 35
<212> TYPE: DNA
<213> ORGANISM: Artificial Sequence
<220> FEATURE:
<223> OTHER INFORMATION: lichApr_F2,

<400> SEQUENCE: 18

```
cctgaagatc cgctgttgag aggaatgccg taagg                               35
```

<210> SEQ ID NO 19
<211> LENGTH: 38
<212> TYPE: DNA
<213> ORGANISM: Artificial Sequence
<220> FEATURE:
<223> OTHER INFORMATION: lichApr_R2

```
<400> SEQUENCE: 19
atgatgagga aaaagagttt ttggcttggg atgctgac                               38

<210> SEQ ID NO 20
<211> LENGTH: 37
<212> TYPE: DNA
<213> ORGANISM: Artificial Sequence
<220> FEATURE:
<223> OTHER INFORMATION: blalich_F1

<400> SEQUENCE: 20
ttattgtgcg ctgtttttcc agttggtcaa attgtcg                                37

<210> SEQ ID NO 21
<211> LENGTH: 36
<212> TYPE: DNA
<213> ORGANISM: Artificial Sequence
<220> FEATURE:
<223> OTHER INFORMATION: blalich_cR1

<400> SEQUENCE: 21
cggacaaggg tcaccaacgg gacaactgtt accatc                                 36

<210> SEQ ID NO 22
<211> LENGTH: 35
<212> TYPE: DNA
<213> ORGANISM: Artificial Sequence
<220> FEATURE:
<223> OTHER INFORMATION: blalich_cF2

<400> SEQUENCE: 22
gatggtaaca gttgtcccgt tggtgaccct tgtcc                                  35

<210> SEQ ID NO 23
<211> LENGTH: 40
<212> TYPE: DNA
<213> ORGANISM: Artificial Sequence
<220> FEATURE:
<223> OTHER INFORMATION: blalich_R2

<400> SEQUENCE: 23
cggcgttggt tagtaaaaag agtgttaaac gaggtttgat                             40
```